(12) United States Patent
Eriksson et al.

(10) Patent No.: US 6,706,687 B1
(45) Date of Patent: Mar. 16, 2004

(54) PLATELET-DERIVED GROWTH FACTOR D

(75) Inventors: Ulf Eriksson, Stockholm (SE); Karin Aase, Stockholm (SE); Xuri Lee, Stockholm (SE); Annica Ponten, Stockholm (SE); Marko Uutela, Helsinki (FI); Kari Alitalo, Helsinki (FI); Arne Oestman, Uppsala (SE); Carl-Henrik Heldin, Uppsala (SE)

(73) Assignees: Ludwig Institute for Cancer Research, New York, NY (US); Helsinki University, Helsinki (FI)

( * ) Notice: Subject to any disclaimer, the term of this patent is extended or adjusted under 35 U.S.C. 154(b) by 0 days.

(21) Appl. No.: 09/438,046

(22) Filed: Nov. 10, 1999

Related U.S. Application Data

(60) Provisional application No. 60/107,852, filed on Nov. 10, 1998, provisional application No. 60/113,997, filed on Dec. 28, 1998, provisional application No. 60/150,604, filed on Aug. 26, 1999, provisional application No. 60/157,108, filed on Oct. 4, 1999, and provisional application No. 60/157,756, filed on Oct. 5, 1999.

(51) Int. Cl.$^7$ ........................ C07K 14/49; C12N 15/16; A61K 38/18
(52) U.S. Cl. ........................ 514/12; 530/399; 530/350; 536/23.5; 536/23.51
(58) Field of Search ................ 435/69.1, 69.5; 514/2, 4, 12; 530/350, 399; 536/23.1, 23.4, 23.5, 23.51

(56) References Cited

U.S. PATENT DOCUMENTS 5,607,918 A 3/1997 Eriksson et al.
5,665,567 A * 9/1997 Eichner et al. ............ 435/69.4

FOREIGN PATENT DOCUMENTS

WO    WO 96/27007    9/1996

OTHER PUBLICATIONS

Mikayama et al. Moleuclar cloning and functional expression of cDNA encoding glycosylation–inhibiting factor. 1993, Proc Natl Acad Sci USA. vol. 90, pp. 10056–10060.*
Voet et al. Biochemistry, John Wiley & Sons, Inc. pp. 126–128, and 228–234.*
Database GENCORE on EST, AN AA488780, NCI–CGAP, National Cancer Institute, Cancer Genome Anatomy Project (CGAP), Tumor Gene Index, Gene Sequence, Aug. 15, 1997.
Database GENCORE on EST, AN AA488996, NCI–CGAP, National Cancer Institute, Cancer Genome Anatomy Project (CGAP), tumor Gene Index, Gene Sequence, Aug. 15, 1997.
Database GENCORE on EST, AN AA 736766, NCI–CGAP, National Cancer Institute, Cancer Genome Anatomy Project (CGAP), Tumor Gene Index, Gene Sequence, Jan. 23, 1998.
Database GENCORE on EST, AN AQ041639, Adams et al. Use of a random BAC End Sequence Database for Sequence–Ready Map Building (1998), Gene Sequence, Jul. 14, 1998.
Copy of International Search Report, Apr. 25, 2000.

* cited by examiner

*Primary Examiner*—Prema Mertz
(74) *Attorney, Agent, or Firm*—Crowell & Moring LLP

(57) ABSTRACT

PDGF-D, a new member of the PDGF/VEGF family of growth factors, is described, as well as the nucleotide sequence encoding it, methods for producing it, antibodies and other antagonists to it, transfected and transformed host cells expressing it, pharmaceutical compositions containing it, and uses thereof in medical and diagnostic applications.

22 Claims, 21 Drawing Sheets aattgtggct gtggaactgt caactggagg tcctgcacat gcaattcagg gaaaaccgtg 60
aaaaagtatc atgaggtatt acagtttgag cctggccaca tcaagaggag gggtagagct 120
aagaccatgg ctctagttga catccagttg gatcaccatg aacgatgtga ttgtatctgc 180
agctcaagac cacctcgata agagaatgtg cacatcctta cattaagcct gaaagaacca 240
ttagtttaag gagggtgaga taagagaccc ttttcctacc agcaaccaga cttactacta 300
gcctgcaatg caatgaacac aagtggttgc tgagtctcat ccttgctttg ttaatgccat 360

FIG.1

Asn Cys Gly Cys Gly Thr Val Asn Trp Arg Ser Cys Thr Cys Asn Ser
 1           5                  10                  15

Gly Lus Thr Val Lys Lys Tyr His Glu Val Leu Gln Phe Glu Pro Gly
              20                  25                  30

His Ile Lys Arg Arg Gly Arg Ala Lys Thr Met Ala Leu Val Asp Ile
              35                  40                  45

Gln Leu Asp His His Glu Arg Cys Asp Cys Ile Cys Ser Ser Arg Pro
              50                  55                  60

Pro Arg
65

FIG.2

```
ggaagatttc caacccgcag cagcttcaga gaccaactgg aatctgtcac aagctctgtt  60
tcagggtatc cctataactc tccatcagta acggatccca ctctgattgc ggatgctctg 120
gacaaaaaaa ttgcagaatt tgatacagtg gaagatctgc tcaagtactt caatccagag 180
tcatggcaag aafatcttga gaatatgtat ctggacaccc ctcggtatcg aggcaggtca 240
taccatgacc ggaagtcaaa agttgacctg gataggctca atgatgatgc caagcgttac 300
agttgcactc ccaggaatta ctcggtcaat ataagagaag agctgaagtt ggccaatgtg 360
gtcttctttc cacgttgcct cctcgtgcag cgctgtggag gaaattgtgg ctgtggaact 420
gtcaaactgg agtcctgcac atgcaattca gggaaaaccg tgaaaaagta tcatgaggta 480
ttacagtttg agcctggcca catcaagagg aggggtagag ctaagaccat ggctctagtt 540
gacatccagt tggatcacca tgaacgatgc gattgtatct gcagctcaag accacctcga 600
taagagaatg tgcacatcct tacattaagc ctgaaagaac ctttagttta aggagggtga 660
gataagagac cctttttccta ccagcaaccc                                  690
```

FIG.3

Gly Arg Phe Pro Thr Arg Ser Ser Phe Arg Asp Gln Leu Glu Ser Val
1               5                       10                  15

Thr Ser Ser Val Ser Gly Tyr Pro Tyr Asn Ser Pro Ser Val Thr Asp
                20              25                  30

Pro Thr Leu Ile Ala Asp Ala Leu Asp Lys Lys Ile Ala Glu Phe Asp
            35                  40                  45

Thr Val Glu Asp Leu Leu Lys Tyr Phe Asn Pro Glu Ser Trp Gln Glu
    50                  55                  60

Asp Leu Glu Asn Met Tyr Leu Asp Thr Pro Arg Tyr Arg Gly Arg Ser
65              70                  75                      80

Tyr His Asp Arg Lys Ser Lys Val Asl Leu Asp Arg Leu Asn Asp Asp
                85                  90                  95

Ala Lys Arg Tyr Ser Cys Thr Pro Arg Asn Tyr Ser Val Asn Ile Arg
            100             105                 110

Glu Glu Leu Lys Leu Ala Asn Val Val Phe Phe Pro Arg Cys Leu Leu
            115                 120                 125

Val Gln Arg Cys Gly Gly Asn Cys Gly Cys Gly Thr Val Lys Leu Glu
        130             135                 140

Ser Cys Thr Cys Asn Ser Gly Lys Thr Val Lys Lus Tyr His Glu Val
145                 150                 155                 160

Leu Gln Phe Glu Pro Gly His Ile Lys Arg Arg Gly Arg Ala Lys Thr
                165                 170                 175

Met Ala Leu Val Asp Ile Gln Leu Asp His His Glu Arg Cys Asp Cys
            180                 185                 190

Ile Cys Ser Ser Arg Pro Pro Arg
            195         200

FIG.4

```
ttgtaccgaa gagatgagac catccaggtg aaaggaaacg gctacgtgca gagtcctaga   60
ttcccgaaca gctacccag gaacctgctc ctgacatggc ggcttcactc tcaggagaat  120
acacggatac agctagtgtt tgacaatcag tttggattag aggaagcaga aaatgatatt  180
tgtaggtatg attttgtgga agttgaagat atatccgaaa ccagtaccat tattagagga  240
cgatggtgtg gacacaagga agttcctcca aggataaaat caagaacgaa ccaaattaaa  300
atcacattca agtccgatga ctactttgtg gctaaacctg gattcaagat ttattattct  360
ttgctggaag attccaacc cgcagcagct tcagagacca actgggaatc tgtcacaagc  420
tctatttcag gggtatccta taactctcca tcagtaacgg atcccacrcr gattfcffat  480
gctctggaca aaaaaattgc agaatttgat acagtggaag atctgctcaa gtacttcaat  540
ccagagtcat ggcaagaaga tcttgagaat atgtatctgg acaccccctcg gtattgaggc  600
aggtcatacc atgaccggaa gtcaaaagtt gacctggata ggctcaatga tgatgccaag  660
cgttacagtt gcactcccag gaattactcg gtcaatataa gagaagagct gaagttggcc  720
aatgtggtct tctttccacg ttgcctcctc gtgcagcgct gtggaggaaa ttgtggctgt  780
ggaactgtca actggaggtc ctgcacatgc aattcaggga aaaccgtgaa aaagtatcat  840
gaggtattac agtttgagcc tggccacatc aagaggaggg gtagagctaa gaccatggct  900
ctagttgaca tccagttgga tcaccatgaa cgatgcgatt gtatctgcag ctcaagacca  960
cctcgataag agaatgtgca catccttaca ttaagcctga aagaaccttt agtttaagga 1020
gggtgagata agagaccctt ttcctaccag caaccaaact tactactagc ctgcaatgca 1080
atgaacacaa gtggttgctg agtctcagcc ttgctttgtt aatgccatgg caagtagaaa 1140
ggtatatcat caacttctat acctaagaat ataggattgc atttaataat agtgtttgag 1200
gttatatatg cacaaacaca cacagaaata tattcatgtc tatgtgtata tagtcaaat 1260
gttttttttg gtatatataa ccaggtacac cagagcttac atatgtttga gttagactct 1320
taaaatcctt tgccaaaata agggatggtc aaatatatga aacatgtctt tagaaaattt 1380
aggagataaa tttattttta aattttgaaa cacaaaacaa ttttgaatct tgctctctta 1440
aagaaagcat cttgtatatt aaaaatcaaa agatgaggct ttcttacata tacatcttag 1500
ttgattatta aaaaaggaaa aaggtttcca gagaaaaggc caataccctaa gcattttttc 1560
catgagaagc actgcatact tacctatgtg gactgtaata acctgtctcc aaaaccatgc 1620
cataataata taagtgcttt agaaattaaa tcattgtgtt ttttatgcat tttgctgagg 1680
catccttatt catttaacac ctatctcaaa aacttactta gaaggttttt tattatagtc 1740
ctacaaaaga caatgtataa gctgtaacag aattttgaat tgttttttctt tgcaaaaccc 1800
ctccacaaaa gcaaatcctt tcaagaatgg catgggcatt ctgtatgaac ctttccagat 1860
ggtgttcagt gaaagatgtg ggtagttgag aacttaaaaa gtgaacattg aaacatcgac 1920
gtaactggaa accg                                                   1934
```

FIG.5

Leu Tyr Arg Arg Asp Glu Thr Ile Gln Val Lys Gly Asn Gly Tyr Val
1            5                    10                  15
Gln Ser Pro Arg Phe Pro Asn Ser Tyr Pro Arg Asn Leu Leu Leu Thr
            20                  25                  30
Trp Arg Leu His Ser Gln Glu Asn Thr Arg Ile Gln Leu Val Phe Asp
        35                  40                  45
Asn Gln Phe Gly Leu Glu Glu Ala Glu Asn Asp Ile Cys Arg Tyr Asp
    50                  55                  60
Phe Val Glu Val Glu Asp Ile Ser Glu Thr Ser Thr Ile Ile Arg Gly
65                  70                  75                  80
Arg Trp Cys Gly His Lys Glu Val Pro Pro Arg Ile Lys Ser Arg Thr
            85                  90                  95
Asn Gln Ile Lus Ile Thr Phe Lys Ser Asp Asp Tyr Phe Val Ala Lys
            100                 105                 110
Pro Gly Phe Lys Ile Tyr Tyr Ser Leu Leu Glu Asp Phe Gln Pro Ala
            115                 120                 125
Ala Ala Ser Glu Thr Asn Trp Glu Ser Val Thr Ser Ser Ile Ser Gly
            130                 135                 140
Val Ser Try Asn Ser Pro Ser Val The Asp Pro Thr Lei Ile Ala Asp
145                 150                 155                 160
Ala Leu Asp Lys Lys Ile Ala Glu Phe Asp The Val Glu Asp Leu Leu
                165                 170                 175
Lys Tyr Phe Asn Pro Glu Ser Trp Gln Glu Asp Leu Glu Asn Met Tyr
            180                 185                 190
Leu Asp Thr Pro Arg Tyr Arg Gly Arn Ser Tyr His Asp Arg Lys Ser
            195                 200                 205
Lys Val Asp Leu Asp Arg Leu Asn Asp Asp Ala Lys Arg Tyr Ser Cys
            210                 215                 220

FIG. 6A

Thr Pro Arg Asn Tyr Ser Val Asn Ile Arg Glu Glu Leu Lus Leu Ala
225                 230                 235                 240
Asn Val Val Phe Phe Pro Arg Cys Leu Leu Val Gln Arg Cys Asn Ser
            245                 250                 255
Asn Cys Gly Cys Gly Thr Val Asn Trp Arg Ser Cys Thr Cys Asn Ser
            260                 265                 270
Gly Lys Thr Val Lys Lys Tyr His Glu Val Leu Gln Phe Glu Pro Gly
        275                 280                 285
Hil Ile Lys Arg Arg Gly Arg Ala Lys Thr Met Ala Leu Val Asp Ile
        290                 295                 300
Gln Leu Asp His His Glu Arg Cys Asp Cys Ile Cus Ser Ser Arg Pro
305                 310                 315                 320
Pro Arg

FIG. 6B

```
cgctcggaaa gttcagcatg caggaagttt ggggagagct cggcgattag cacagcgacc  60
cgggccagcg cagggcgagc gcaggcggcg agagcgcagg gcggcgcggc gtcggtcccg 120
ggagcagaac ccggcttttt cttggagcga cgctgtctct agtcgctgat cccaa       175
```

| atg | cac | cgg | ctc | atc | ttt | gtc | tac | act | cta | atc | tgc | gca | aac | ttt | tgc | 223 |
|---|---|---|---|---|---|---|---|---|---|---|---|---|---|---|---|---|
| Mat | His | Arg | Leu | Ile | Phe | Val | Tyr | Thr | Leu | Ile | Cys | Ala | Asn | Phe | Cys | |
| 1 | | | | 5 | | | | | 10 | | | | | 15 | | |

| agc | tgt | cgg | gac | act | tct | gca | acc | ccg | cag | agc | gca | tcc | atc | aaa | gct | 271 |
|---|---|---|---|---|---|---|---|---|---|---|---|---|---|---|---|---|
| Ser | Cys | Arg | Asp | The | Ser | Ala | Thr | Pro | Gln | Ser | Ala | Ser | Ile | Lus | Ala | |
| | | | 20 | | | | | 25 | | | | | 30 | | | |

| ttg | cgc | aac | gcc | aac | ctc | agg | cga | gat | gag | agc | aat | cac | ctc | aca | gac | 319 |
|---|---|---|---|---|---|---|---|---|---|---|---|---|---|---|---|---|
| Leu | Arg | Asn | Ala | Asn | Leu | Arg | Arg | Asp | Glu | Ser | Asn | His | Leu | Thr | Asp | |
| | | 35 | | | | | 40 | | | | | 45 | | | | |

| ttg | tac | cga | aga | gat | gag | acc | atc | cag | gtg | aaa | gga | aac | ggc | tac | gtg | 367 |
|---|---|---|---|---|---|---|---|---|---|---|---|---|---|---|---|---|
| Leu | Tyr | Arg | Arg | Asp | Glu | Thr | Ile | Gln | Val | Lys | Gly | Asn | Gly | Tyr | Val | |
| | 50 | | | | | 55 | | | | | 60 | | | | | |

| cag | agt | cct | aga | ttc | ccg | aac | agc | tac | ccc | agg | aac | ctg | ctc | ctg | aca | 415 |
|---|---|---|---|---|---|---|---|---|---|---|---|---|---|---|---|---|
| Gln | Ser | Pro | Arg | Phe | Pro | Asn | Ser | Tyr | Pro | Arg | Asn | Leu | Leu | Leu | Thr | |
| 65 | | | | | 70 | | | | | 75 | | | | | 80 | |

| tgg | cgg | ctt | cac | tct | cag | gag | aat | aca | cgg | ata | cat | cta | gtg | ttt | gac | 463 |
|---|---|---|---|---|---|---|---|---|---|---|---|---|---|---|---|---|
| Trp | Arg | Leu | His | Ser | Gln | Glu | Asn | Thr | Arg | Ile | Gln | Leu | Val | Phe | Asp | |
| | | | | 85 | | | | | 90 | | | | | 95 | | |

| aat | cag | ttt | gga | tta | gag | gaa | gca | gaa | aat | gat | atc | tgt | agg | tat | gat | 511 |
|---|---|---|---|---|---|---|---|---|---|---|---|---|---|---|---|---|
| Asn | Gln | Phe | Gly | Leu | Glu | Glu | Ala | Glu | Asn | Asp | Ile | Cys | Arg | Tyr | Asp | |
| | | | 100 | | | | | 105 | | | | | 110 | | | |

| ttt | gtg | gaa | gtt | gaa | gat | ata | tcc | gaa | acc | agt | acc | att | att | aga | gga | 559 |
|---|---|---|---|---|---|---|---|---|---|---|---|---|---|---|---|---|
| Phe | Val | Glu | Val | Glu | Asp | Ile | Ser | Glu | Thr | Ser | The | Ile | Ile | Arg | Gly | |
| | | 115 | | | | | 120 | | | | | 125 | | | | |

| cga | tgg | tgt | gga | cac | aag | gaa | gtt | cct | cca | agg | ata | aaa | tca | aga | acg | 607 |
|---|---|---|---|---|---|---|---|---|---|---|---|---|---|---|---|---|
| Arg | Trp | Cys | Gly | His | Lys | Glu | Val | Pro | Pro | Arg | Ile | Lys | Ser | Arg | Thr | |
| | 130 | | | | | 135 | | | | | 140 | | | | | |

| aac | caa | att | aaa | atc | aca | ttc | aag | tcc | gat | gac | tac | ttt | gtg | gct | aaa | 655 |
|---|---|---|---|---|---|---|---|---|---|---|---|---|---|---|---|---|
| Asn | Gln | Ile | Lys | Ile | Thr | Phe | Pys | Ser | Asp | Asp | Tyr | Phe | Val | Ala | Lys | |
| 145 | | | | | 150 | | | | | 155 | | | | | 160 | |

FIG. 7A

```
cct gga ttc aag att tat tat tct ttg ctg gaa gat ttc caa ccc gca    703
Fro Gly Phe Lys Ile Tyr Tyr Ser Leu Leu Glu Asp Phe Gln Pro Ala
            165             170             175 gca gct tta gag acc aac tgg gaa tct gtc aca agc tct att tca ggg    751
Ala Ala Ser Glu Ths Asn Trp Glu Ser Val Thr Ser Ser Ile Ser Gly
            180             185             190 gta tcc tat aac tct cca tca gta act gat ccc act ctg att gag gat    799
Val Ser Tyr Asn Ser Pro Ser Val Thr Asp Pro Thr Leu Ile Ala Asp
            195             200             205 gct ctg gac aaa aaa att gca gaa ttt gat aca gtg gaa gat ctg ctc    847
Ala Leu Asp Lys Lys Ile Ala Glu Phe Asp Thr Val Glu Asp Leu Lei
            210             215             220 aag tac ttc aat cca gag tca tgg caa gaa gat ctt gag aat atg tat    895
Lys thr Phe Asn Pro Glu Ser Trp Gln Glu Asp Leu Flu Asn Met Tyr
225             230             235             240 ctg gac acc cct cgg tat cga ggc agg tca tac cat gac cgg aag tca    943
Leu Asp Thr Pro Arg Tyr Arg Gly Arg Ser Tyr His Asp Arg Lys Ser
            245             250             255 aaa gtt gac ctg gat agg ctc aat gat gat gcc aag cgt tac agt tgc    991
Lys Val Asl Leu Asp Arg Leu Asn Asp Asp Ala Lus Arg Tyr Ser Cys
            260             265             270 act ccc agg aat tac tcg gtc aat ata aga gaa gag ctg aag ttg gcc    1039
Thr Pro Arg Asn Try Ser Val Asn Ils Arg Glu Glu Leu Lys Leu Ala
            275             280             285 aat gtg gtc ttc ttt cca cgt tgc ctc ctc gtg cag cgc tgt gga gga    1087
Asn Val Val Phe Phe Pro Arg Cys Leu Leu Val Gln Arg Cys Gly Gly
            290             295             300 aat tgt ggc tgt gga act gtc aac tgg agg tcc tgc aca tgc aat tca    1135
Asn Cys Gly Cys Gly Thr Val Asn Trg Arg Ser Cys Thr Cys Asn Ser
305             310             315             320 ggg aaa acc gtg aaa aag tat cat gag gta tta cag ttt gag cct ggc    1183
Gly Lys Thr Val Lys Lys Tyr His Glu Val Leu Gln Phe Glu Pro Gly
            325             330             335
```

FIG. 7B cac atc aag agg agg ggt aga gct aag acc atg gct cta gtt gac atc    1231
His Ile Lys Arg Arg Gly Arg Ala Lys Thr Met Ala Leu Val Asp Ile
         340             345             350 cag ttg gat cac cat gaa cga tgc gat tgt atc tgc agc tca aga cca    1279
Gln Leu Asp His His Glu Arg Cys Asp Cys Ile Cys Ser Ser Arg Pro
         355             360             365 cct cga taagagaatg tgcacatcct tacattaagc ctgaagaac ctttagttta      1335
Pro Arg
   370 aggagggtga gataagagac ccttttccta ccagcaacca aacttactac tagcctgcaa 1396
tgcaatgaac acaagtggtt gctgagtctc agccttgctt tgttaatgcc atggcaagta 1455
gaaaggtata tcatcaactt ctatacctaa gaatatagga ttgcatttaa taatagtgtt 1515
tgaggttata tatgcacaaa cacacacaga aatatattca tgtctatgtg tatatagatc 1575
aaatgttttt tttggtatat ataaccaggt acaccagagc ttacatatgt ttgagttaga 1635
ctcttaaaat ccttgccaa aataagggat ggtcaaatat atgaaacatg tctttagaaa 1695
atttaggaga taaatttatt tttaaatttt gaaacacaaa acaattttga atcttgctct 1755
cttaaagaaa gcatcttgta tattaaaaat caaaagatga ggctttctta catatacatc 1815
ttagttgatt attaaaaaag gaaaaaggtt tccagagaaa aggccaatac ctaagcattt 1875
tttccatgag aagcactgca tacttaccta tgtggactgt aataacctgt ctccaaaacc 1935
atgccataat aatataagtg cttagaaat taaatcattg tgttttttat gcattttgct 1995
gaggcatcct tattcattta acacctatct caaaaactta cttagaaggt ttttattat 2055
agtcctacaa aagacaatgt ataagctgta acagaatttt gaattgtttt tctttgcaaa 2115
accccctccac aaaagcaaat ccttcaaga atggcatggg cattctgtat gaacctttcc 2175
agatggtgtt cagtgaaaga tgtgggtagt tgagaactta aaaagtgaac attgaaacat 2235
cgacgtaact ggaaaccg............................................. 2253

FIG. 7C

```
Met His Arg Leu Ile Phe Val Tyr Thr Leu Ile Cys Ala Asn Phe
 1               5                   10                  15
Cys Ser Cys Arg Asp Thr Ser Ala Thr Pro Gln Ser Ala Ser Ile Lys
                 20                  25                  30
Ala Leu Arg Asn Ala Asn Leu Arf Arg Asp Glu Ser Asn His Leu Thr
             35                  40                  45
Asp Leu Tyr Arg Arg Asp Glu Thr Ile Gln Val Lys Gly Asn Gly Tyr
             50                  55                  60
Val Gln Ser Pro Arg Phe Pro Asn Ser Tyr Pro Arg Asn Leu Leu Leu
 65                  70                  75
Thr Trp Arg Leu His Ser Gln Glu Asn Thr Arg Ile Gln Leu Val Phe
 80                  85                  90                  95
Asp Asn Gln Phe Gly Leu Glu Glu Ala Glu Asn Asp Ile Cys Arg Tyr
                 100                 105                 110
Asp Phe Val Glu Val Glu Asp Ile Ser Glu Thr Ser Thr Ile Ile Arg
                 115                 120                 125
Gly Arg Trp Cys Gly His Lys Glu Val Pro Pro Arg Ile Lys Ser Arg
                 130                 135                 140
Thr Asn Gln Ile Lys Ile Thr Phe Lys Ser Asp Asp Tyr Phe Val Ala
                 145                 150                 155
Lys Pro Gly Phe Lys Ile Tyr Tyr Ser Leu Leu Glu Asp Phe Gln Pro
160                  165                 170                 175
Ala Ala Ala Ser Glu Thr Asn Trp Glu Ser Val Thr Ser Ser Ile Ser
                 180                 185                 190
Gly Val Ser Tyr Asn Ser pro Ser Val Thr Asp Pro Thr Leu Ile Ala
                 195                 200                 205
Asp Ala Leu Asp Lys Lys Ile Ala Glu Phe Asp Thr Val Glu Asp Leu
                 210                 215                 220
Leu Lys Thr Phe Asn Pro Glu Ser trp Gln Glu Asp Leu Glu Asn Met
                 225                 230                 235
```

FIG. 8A

Tyr Leu Asn Thr Pro Arg Tyr Arg Gly Arg Ser Tyr His Asp Arg Lys
240             245             250             255
Ser Lys Val Asp Leu Asp Arg Leu Asn Asp Asp Ala Lys Arg Tyr Ser
            260             265             270
Cys Thr Pro Arg Asn Tyr Ser Val Asn Ile Arg Glu Glu Leu Lys Leu
            275             280             285
Ala Asn Val Val Phe Phe Pro Arg Cys Leu Leu Val Gln Arg Cys Gly
            290             295             300
Gly Asn Cys Gly Cys Gly Thr Val Asn Trp Arg Ser Cys Thr Cys Asn
        305             310             315
Ser Gly Lys Thr Val Lys Lys Tyr His Glu Val Leu Gln Phe Glu Pro
320             325             330             335
Glu His Ile Lys Arg Arg Gly Arg Ala Lys Thr Met Ala Leu Val Asp
            340             345             350
Ile Gln Leu Asp His His Gln Arg Cys Asp Cys Ile Cys Ser Ser Arg
            355             360             365
Pro Pro Arg
    370

FIG. 8B

```
VEGF 165     ------------------------------------------------------------    1
PlGF-2       ------------------------------------------------------------    1
VEGF-B167    ------------------------------------------------------------    1
Pox Orf VEGF ------------------------------------------------------------    1
VEGF-C       MHLLGFFSVACSLLAAALLPGPREAPAAAAFESGLDLSD                          40
VEGF-D       ------------------------MYGEWGMGNILMMFHVYLVQGFRSF                25
PCGF-A       ------------------------------MRTLAC                              6
PCGF-B       ------------------------------MNRCWALFLS                         10
hPCGF-D      ------------------------------------------------------------  202

VEGF 165     ------------------------------------------------------------    1
PlGF-2       ------------------------------------------------------------    1
VEGF-A167    ------------------------------------------------------------    1
Pox Orf VEGF ------------------------------------------------------------    1
VEGF-C       AEPDAGEATAYASKDLEEQLRSVSSVDELMTVLYPEYWKM                         80
VEGF-D       KGPVKDFSFERSSRSMLERSEQQIRAASSLEELLQIAHSS                         65
PCGF-A       LLLGCGYLAHVLAEEAEIPREVIERLARSQIHSIRDLQR                          46
PCGF-B       LCCYLRLVSAEGDPIPEELYEMLSDHSIRSFDDLDRLLHG                         50
hPCGF-D      ------------------------------------------------------------  202
```

```
VEGF 165    D R A R Q E N P C G P C S S E R R K K L F V Q D P Q T C K C S C K N I D S - R C   173
PIGF-2      R R R P K G R G K R R R E N Q R P T D C H L C G L A V P R R                        170
VEGF-B167   K P D S P R P L C P R C T Q H H Q R P D P R T - - C R C R C R R R S P L R C        169
Pox Orf VEGF P P T T R P P R R R                                                              133
VEGF-C      S I I R R S L P A T - L P Q C Q A A N R T C P T N Y M W N N H I C R C L A Q E D   261
VEGF-D      S I I R R S I O I P E E D E C P H S K K L C P I D M L W D N T K C V L O D E       245
PCGF-A      G R P R E S G K K R K R L K P T                                                   211
PCGF-B      G S Q E Q R A K T P Q T R V T I R T V R R P P K G K H R K F K H T H D K T A       234
hPDGF-D                                                                                        322

VEGF 165    K A R Q L E L N E R T C R C D K P R R                                             152
PIGF-2                                                                                         170
VEGF-B167   Q G R G L E L N P D T C R C R K L R R                                             188
Pox Orf VEGF                                                                                  133
VEGF-C      F M F S S D A G D D S T D G F E D I C G P N K E L D E E T C Q C V C R A G L R P   301
VEGF-D      - T P L F G T E D H S Y L O E P T L C G P H M T F D E D R - - - - - - - - -       274
PCGF-A                                                                                         211
PCGF-B      L K E T L G A                                                                     241
hPDGF-D                                                                                        322
```

FIG. 9D

```
VEGF 165     A S C G P H K E L D R N S C Q C V C K N K L F P S Q C G A N R E F D E N T C Q C       192
PlGF-2       - - - - - - - - - - - - - - - - - - - - - - - - - - - - - - - - - - - - - -         170
VEGF-B167    - - - - - - - - - - - - - - - - - - - - - - - - - - - - - - - - - - - - - -         188
Pox Orf VEGF - - - - - - - - - - - - - - - - - - - - - - - - - - - - - - - - - - - - - -         133
VEGF-C                                                                                            341
VEGF-D       - - - - - - - - - - - - - C E C V C K A P C P G D L I Q H P E N - - - C S C         295
PCGF-A       - - - - - - - - - - - - - - - - - - - - - - - - - - - - - - - - - - - - - -         211
PCGF-B       - - - - - - - - - - - - - - - - - - - - - - - - - - - - - - - - - - - - - -         241
hPDGF-D      - - - - - - - - - - - - - - - - - - - - - - - - - - - - - - - - - - - - - -         322

VEGF 165     V C K R T C P R N Q P L N P G K C A C E C T E S P Q K C L L K G K K F H H Q T C       192
PlGF-2       - - - - - - - - - - - - - - - - - - - - - - - - - - - - - - - - - - - - - -         170
VEGF-B167    - - - - - - - - - - - - - - - - - - - - - - - - - - - - - - - - - - - - - -         188
Pox Orf VEGF - - - - - - - - - - - - - - - - - - - - - - - - - - - - - - - - - - - - - -         133
VEGF-C                                                                                            381
VEGF-D       F E C K E S L E S C C Q K H K I - - - - - - - - - - - - - - - - F H P D T C         317
PCGF-A       - - - - - - - - - - - - - - - - - - - - - - - - - - - - - - - - - - - - - -         211
PCGF-B       - - - - - - - - - - - - - - - - - - - - - - - - - - - - - - - - - - - - - -         241
hPDGF-D      - - - - - - - - - - - - - - - - - - - - - - - - - - - - - - - - - - - - - -         322
```

FIG. 9E

```
VEGF 165     S C Y R R P C T N R Q K A C E P G F S Y S E E V C R C V P S Y W K R P Q M S   192
PlGF-2       S C E D R   C P F H T R T C A S R K P F A C G K H W R P K E T R A O G L Y S O E   170
VEGF-B167                                                                                     188
Pox Orf VEGF                                                                                  133
VEGF-C                                                                                        419
VEGF-D                                                                                        356
PCGF-A                                                                                        211
PCGF-B                                                                                        241
hPDGF-D                                                                                       322

VEGF 165                                                                                      192
PlGF-2                                                                                        170
VEGF-B167                                                                                     188
Pox Orf VEGF                                                                                  133
VEGF-C                                                                                        419
VEGF-D                                                                                        352
PCGF-A                                                                                        211
PCGF-B                                                                                        241
hPDGF-D              N P                                                                      322
```

PLATELET-DERIVED GROWTH FACTOR D

CROSS REFERENCE TO RELATED APPLICATIONS

This application claims the benefit of U.S. Provisional Application No. 60/107,852, filed Nov. 10, 1998; U.S. Provisional Application No. 60/113,997, filed Dec. 28, 1998; U.S. Provisional Application No. 60/150,604, filed Aug. 26, 1999; U.S. Provisional Application No. 60/157,108, filed Oct. 4, 1999; and U.S. Provisional Application No. 60/157,756, filed Oct. 5, 1999.

FIELD OF THE INVENTION

This invention relates to growth factors for cells expressing receptors to a novel growth factor that include endothelial cells, connective tissue cells (such as fibroblasts) myofibroblasts and glial cells, and in particular to a novel platelet-derived growth factor/vascular endothelial growth factor-like growth factor, a polynucleotide sequence encoding the factor, and to pharmaceutical and diagnostic compositions and methods utilizing or derived from the factor.

BACKGROUND OF THE INVENTION

In the developing embryo, the primary vascular network is established by in situ differentiation of mesodermal cells in a process called vasculogenesis. It is believed that all subsequent processes involving the generation of new vessels in the embryo and neovascularization in adults, are governed by the sprouting or splitting of new capillaries from the pre-existing vasculature in a process called angiogenesis (Pepper et al., Enzyme & Protein, 1996 49 138–162; Breier et al., Dev. Dyn. 1995 204 228–239; Risau, Nature, 1997 386 671–674). Angiogenesis is not only involved in embryonic development and normal tissue growth, repair, and regeneration, but is also involved in the female reproductive cycle, establishment and maintenance of pregnancy, and in repair of wounds and fractures. In addition to angiogenesis which takes place in the normal individual, angiogenic events are involved in a number of pathological processes, notably tumor growth and metastasis, and other conditions in which blood vessel proliferation, especially of the microvascular system, is increased, such as diabetic retinopathy, psoriasis and arthropathies. Inhibition of angiogenesis is useful in preventing or alleviating these pathological processes.

On the other hand, promotion of angiogenesis is desirable in situations where vascularization is to be established or extended, for example after tissue or organ transplantation, or to stimulate establishment of collateral circulation in tissue infarction or arterial stenosis, such as in coronary heart disease and thromboangitis obliterans.

The angiogenic process is highly complex and involves the maintenance of the endothelial cells in the cell cycle, degradation of the extracellular matrix, migration and invasion of the surrounding tissue and finally, tube formation. The molecular mechanisms underlying the complex angiogenic processes are far from being understood.

Because of the crucial role of angiogenesis in so many physiological and pathological processes, factors involved in the control of angiogenesis have been intensively investigated. A number of growth factors have been shown to be involved in the regulation of angiogenesis; these include fibroblast growth factors (FGFs), platelet-derived growth factor (PDGF), transforming growth factor alpha (TGFα), and hepatocyte growth factor (HGF). See for example Folkman et al., J. Biol. Chem., 1992 267 10931–10934 for a review.

It has been suggested that a particular family of endothelial cell-specific growth factors, the vascular endothelial growth factors (VEGFs), and their corresponding receptors is primarily responsible for stimulation of endothelial cell growth and differentiation, and for certain functions of the differentiated cells. These factors are members of the PDGF family, and appear to act primarily via endothelial receptor tyrosine kinases (RTKs). Nine different proteins have been identified in the PDGF family, namely two PDGFs (A and B), VEGF and six members that are closely related to VEGF. The six members closely related to VEGF are: VEGF-B, described in International Patent Application PCT/US96/02957 (WO 96/26736) and in U.S. Pat. Nos. 5,840,693 and 5,607,918 by Ludwig Institute for Cancer Research and The University of Helsinki; VEGF-C, described in Joukov et al., EMBO J., 1996 15 290–298 and Lee et al., Proc. Natl. Acad. Sci. USA, 1996 93 1988–1992; VEGF-D, described in International Patent Application No. PCT/US97/14696 (WO 98/07832), and Achen et al., Proc. Natl. Acad. Sci. USA, 1998 95 548–553; the placenta growth factor (PlGF), described in Maglione et al., Proc. Natl. Acad. Sci. USA, 1991 88 9267–9271; VEGF2, described in International Patent Application No. PCT/US94/05291 (WO 95/24473) by Human Genome Sciences, Inc; and VEGF3, described in International Patent Application No. PCT/US95/07283 (WO 96/39421) by Human Genome Sciences, Inc. Each VEGF family member has between 30% and 45% amino acid sequence identity with VEGF. The VEGF family members share a VEGF homology domain which contains the six cysteine residues which form the cysteine knot motif. Functional characteristics of the VEGF family include varying degrees of mitogenicity for endothelial cells, induction of vascular permeability and angiogenic and lymphangiogenic properties.

Vascular endothelial growth factor (VEGF) is a homodimeric glycoprotein that has been isolated from several sources. VEGF shows highly specific mitogenic activity for endothelial cells. VEGF has important regulatory functions in the formation of new blood vessels during embryonic vasculogenesis and in angiogenesis during adult life (Carmeliet et al., Nature, 1996 380 435–439; Ferrara et al., Nature, 1996 380 439–442; reviewed in Ferrara and Davis-Smyth, Endocrine Rev., 1997 18 4–25). The significance of the role played by VEGF has been demonstrated in studies showing that inactivation of a single VEGF allele results in embryonic lethality due to failed development of the vasculature (Carmeliet et al., Nature, 1996 380 435–439; Ferrara et al., Nature, 1996 380 439–442). In addition VEGF has strong chemoattractant activity towards monocytes, can induce the plasminogen activator and the plasminogen activator inhibitor in endothelial cells, and can also induce microvascular permeability. Because of the latter activity, it is sometimes referred to as vascular permeability factor (VPF). The isolation and properties of VEGF have been reviewed; see Ferrara et al., J. Cellular Biochem., 1991 47 211–218 and Connolly, J. Cellular Biochem., 1991 47 219–223. Alterative mRNA splicing of a single VEGF gene gives rise to five isoforms of VEGF.

VEGF-B has similar angiogenic and other properties to those of VEGF, but is distributed and expressed in tissues differently from VEGF. In particular, VEGF-B is very strongly expressed in heart, and only weakly in lung, whereas the reverse is the case for VEGF. This suggests that VEGF and VEGF-B, despite the fact that they are co-expressed in many tissues, may have functional differences.

VEGF-B was isolated using a yeast co-hybrid interaction trap screening technique by screening for cellular proteins which might interact with cellular resinoid acid-binding protein type I (CRABP-I). Its isolation and characteristics are described in detail in PCT/US96/02957 and in Olofsson et al., Proc. Natl. Acad. Sci. USA, 1996 93 2576–2581.

VEGF-C was isolated from conditioned media of the PC-3 prostate adenocarcinoma cell line (CRL1435) by screening for ability of the medium to produce tyrosine phosphorylation of the endothelial cell-specific receptor tyrosine kinase VEGFR-3 (Flt4), using cells transfected to express VEGFR-3. VEGF-C was purified using affinity chromatography with recombinant VEGFR-3, and was cloned from a PC-3 cDNA library. Its isolation and characteristics are described in detail in Joukov et al., EMBO J., 1996 15 290–298.

VEGF-D was isolated from a human breast cDNA library, commercially available from Clontech, by screening with an expressed sequence tag obtained from a human cDNA library designated "Soares Breast 3NbHBst" as a hybridization probe (Achen et al., Proc. Natl. Acad. Sci. USA, 1998 95 548–553). Its isolation and characteristics are described in detail in International Patent Application No. PCT/US97/14696 (WO98/07832).

The VEGF-D gene is broadly expressed in the adult human, but is certainly not ubiquitously expressed. VEGF-D is strongly expressed in heart, lung and skeletal muscle. Intermediate levels of VEGF-D are expressed in spleen, ovary, small intestine and colon, and a lower expression occurs in kidney, pancreas, thymus, prostate and testis. No VEGF-D mRNA was detected in RNA from brain, placenta, liver or peripheral blood leukocytes.

PlGF was isolated from a term placenta cDNA library. Its isolation and characteristics are described in detail in Maglione et al., Proc. Natl. Acad. Sci. USA, 1991 88 9267–9271. Presently its biological function is not well understood.

VEGF2 was isolated from a highly tumorgenic, oestrogen-independent human breast cancer cell line. While this molecule is stated to have about 22% homology to PDGF and 30% homology to VEGF, the method of isolation of the gene encoding VEGF2 is unclear, and no characterization of the biological activity is disclosed.

VEGF3 was isolated from a cDNA library derived from colon tissue. VEGF3 is stated to have about 36% identity and 66% similarity to VEGF. The method of isolation of the gene encoding VEGF3 is unclear and no characterization of the biological activity is disclosed.

Similarity between two proteins is determined by comparing the amino acid sequence and conserved amino acid substitutions of one of the proteins to the sequence of the second protein, whereas identity is determined without including the conserved amino acid substitutions.

PDGF/VEGF family members act primarily by binding to receptor tyrosine kinases. Five endothelial cell-specific receptor tyrosine kinases have been identified, namely VEGFR-1 (Flt-1), VEGFR-2 (KDR/Flk-1), VEGFR-3 (Flt4), Tie and Tek/Tie-2. All of these have the intrinsic tyrosine kinase activity which is necessary for signal transduction. The essential, specific role in vasculogenesis and angiogenesis of VEGFR-1, VEGFR-2, VEGFR-3, Tie and Tek/Tie-2 has been demonstrated by targeted mutations inactivating these receptors in mouse embryos.

The only receptor tyrosine kinases known to bind VEGFs are VEGFR-1, VEGFR-2 and VEGFR-3. VEGFR-1 and VEGFR-2 bind VEGF with high affinity, and VEGFR-1 also binds VEGF-B and PlGF. VEGF-C has been shown to be the ligand for VEGFR-3, and it also activates VEGFR-2 (Joukov et al., The EMBO Journal, 1996 15 290–298).

VEGF-D binds to both VEGFR-2 and VEGFR-3. A ligand for Tek/Tie-2 has been described in International Patent Application No. PCT/US95/12935 (WO 96/11269) by Regeneron Pharmaceuticals, Inc. The ligand for Tie has not yet been identified.

Recently, a novel 130–135 kDa VEGF isoform specific receptor has been purified and cloned (Soker et al., Cell, 1998 92 735–745). The VEGF receptor was found to specifically bind the $VEGF_{165}$ isoform via the exon 7 encoded sequence, which shows weak affinity for heparin (Soker et al., Cell, 1998 92 735–745). Surprisingly, the receptor was shown to be identical to human neuropilin-1 (NP-1), a receptor involved in early stage neuromorphogenesis. PlGF-2 also appears to interact with NP-1 (Migdal et al., J. Biol. Chem., 1998 273 22272–22278).

VEGFR-1, VEGFR-2 and VEGFR-3 are expressed differently by endothelial cells. Both VEGFR-1 and VEGFR-2 are expressed in blood vessel endothelia (Oelrichs et al., Oncogene, 1992 8 11–18; Kaipainen et al., J. Exp. Med., 1993 178 2077–2088; Dumont et al., Dev. Dyn., 1995 203 80–92; Fong et al., Dev. Dyn., 1996 207 1–10) and VEGFR-3 is mostly expressed in the lymphatic endothelium of adult tissues (Kaipainen et al., Proc. Natl. Acad. Sci. USA, 1995 9 3566–3570). VEGFR-3 is also expressed in the blood vasculature surrounding tumors.

Disruption of the VEGFR genes results in aberrant development of the vasculature leading to embryonic lethality around midgestation. Analysis of embryos carrying a completely inactivated VEGFR-1 gene suggests that this receptor is required for functional organization of the endothelium (Fong et al., Nature, 1995 376 66–70). However, deletion of the intracellular tyrosine kinase domain of VEGFR-1 generates viable mice with a normal vasculature (Hiratsuka et al., Proc. Natl. Acad. Sci. USA 1998 95 9349–9354). The reasons underlying these differences remain to be explained but suggest that receptor signalling via the tyrosine kinase is not required for the proper function of VEGFR-1. Analysis of homozygous mice with inactivated alleles of VEGFR-2 suggests that this receptor is required for endothelial cell proliferation, hematopoesis and vasculogenesis (Shalaby et al., Nature, 1995 376 62–66; Shalaby et al., Cell, 1997 89 981–990). Inactivation of VEGFR-3 results in cardiovascular failure due to abnormal organization of the large vessels (Dumont et al. Science, 1998 282 946–949).

Although VEGFR-1 is mainly expressed in endothelial cells during development, it can also be found in hematopoetic precursor cells during early stages of embryogenesis (Fong et al., Nature, 1995 376 66–70). It is also is expressed by most, if not all, vessels in embryos (Breier et al., Dev. Dyn., 1995 204 228–239; Fong et al., Dev. Dyn., 1996 207 1–10). In adults, monocytes and macrophages also express this receptor (Barleon et al., Blood, 1996 87 3336–3343).

The receptor VEGFR-3 is widely expressed on endothelial cells during early embryonic development, but as embryogenesis proceeds, it becomes restricted to venous endothelium and then to the lymphatic endothelium (Kaipainen et al., Cancer Res., 1994 54 6571–6577; Kaipainen et al., Proc. Natl. Acad. Sci. USA, 1995 92 3566–3570). VEGFR-3 continues to be expressed on lymphatic endothelial cells in adults. This receptor is essential for vascular development during embryogenesis. Targeted inactivation of both copies of the VEGFR-3 gene in mice resulted in defective blood vessel formation characterized by abnormally organized large vessels with defective lumens, leading to fluid accumulation in the pericardial cavity and cardiovascular failure at post-coital day 9.5. On the basis of these findings it has been proposed that VEGFR-3 is required for the maturation of primary vascular networks into larger blood vessels. However, the role of VEGFR-3 in the development of the lymphatic vasculature could not be studied in these mice because the embryos died before the lymphatic system emerged.

Nevertheless it is assumed that VEGFR-3 plays a role in development of the lymphatic vasculature and lymphangiogenesis given its specific expression in lymphatic endothelial cells during embryogenesis and adult life. This is supported by the finding that ectopic expression of VEGF-C, a ligand for VEGFR-3, in the skin of transgenic mice, resulted in lymphatic endothelial cell proliferation and vessel enlargement in the dermis. Furthermore this suggests that VEGF-C may have a primary function in lymphatic endothelium, and a secondary function in angiogenesis and permeability regulation which is shared with VEGF (Joukov et al., EMBO J., 1996 15 290–298).

Some inhibitors of the VEGF/VEGF-receptor system have been shown to prevent tumor growth via an anti-angiogenic mechanism; see Kim et al., Nature, 1993 362 841–844 and Saleh et al., Cancer Res., 1996 56 393–401.

As mentioned above, the VEGF family of growth factors are members of the PDGF family. PDGF plays a important role in the growth and/or motility of connective tissue cells, fibroblasts, myofibroblasts and glial cells (Heldin et al., "Structure of platelet-derived growth factor: Implications for functional properties", Growth Factor, 1993 8 245–252). In adults, PDGF stimulates wound healing (Robson et al., Lancet, 1992 339 23–25). Structurally, PDGF isoforms are disulfide-bonded dimers of homologous A- and B-polypeptide chains, arranged as homodimers (PDGF-AA and PDGF-BB) or a heterodimer (PDGF-AB).

PDGF isoforms exert their effects on target cells by binding to two structurally related receptor tyrosine kinases (RTKs). The alpha-receptor binds both the A- and B-chains of PDGF, whereas the beta-receptor binds only the B-chain. These two receptors are expressed by many in vitro grown cell lines, and are mainly expressed by mesenchymal cells in vivo. The PDGFs regulate cell proliferation, cell survival and chemotaxis of many cell types in vitro (reviewed in Heldin et al., Biochim Biophys Acta., 1998 1378 F79–113). In vivo, they exert their effects in a paracrine mode since they often are expressed in epithelial (PDGF-A) or endothelial cells (PDGF-B) in close apposition to the PDGFR expressing mesenchyme. In tumor cells and in cell lines grown in vitro, coexpression of the PDGFs and the receptors generate autocrine loops which are important for cellular transformation (Betsholtz et al., Cell, 1984 39 447–57; Keating et al., J. R. Coll Surg Edinb., 1990 35 172–4). Overexpression of the PDGFs have been observed in several pathological conditions, including malignancies, arteriosclerosis, and fibroproliferative diseases (reviewed in Heldin et al., The Molecular and Cellular Biology of Wound Repair, New York: Plenum Press, 1996, 249–273).

The importance of the PDGFs as regulators of cell proliferation and survival are well illustrated by recent gene targeting studies in mice that have shown distinct physiological roles for the PDGFs and their receptors despite the overlapping ligand specificities of the PDGFRs. Homozygous null mutations for either of the two PDGF ligands or the receptors are lethal. Approximately 50% of the homozygous PDGF-A deficient mice have an early lethal phenotype, while the surviving animals have a complex postnatal phenotype with lung emphysema due to improper alveolar septum formation because of a lack of alveolar myofibroblasts (Boström et al., Cell, 1996 85 863–873). The PDGF-A deficient mice also have a dermal phenotype characterized by thin dermis, misshapen hair follicles and thin hair (Karlsson et al., Development, 1999 126 2611–2). PDGF-A is also required for normal development of oligodendrocytes and subsequent myelination of the central nervous system (Fruttiger et al., Development, 1999 126 457–67). The phenotype of PDGFR-alpha deficient mice is more severe with early embryonic death at E10, incomplete cephalic closure, impaired neural crest development, cardiovascular defects, skeletal defects, and odemas (Soriano et al., Development, 1997 124 2691–70). The PDGF-B and PDGFR-beta deficient mice develop similar phenotypes that are characterized by renal, hematological and cardiovascular abnormalities (Leveen et al., Genes Dev., 1994 8 1875–1887; Soriano et al., Genes Dev., 1994 8 1888–96; Lindahl et al., Science, 1997 277 242–5; Lindahl, Development, 1998 125 3313–2), where the renal and cardiovascular defects, at least in part, are due to the lack of proper recruitment of mural cells (vascular smooth muscle cells, pericytes or mesangial cells) to blood vessels (Leveen et al., Genes Dev., 1994 8 1875–1887; Lindahl et al., Science, 1997 277 242–5; Lindahl et al., Development, 1998 125 3313–2).

SUMMARY OF THE INVENTION

The invention generally provides an isolated novel growth factor which has the ability to stimulate and/or enhance proliferation or differentiation and/or growth and/or motility of cells expressing a PDGF-D receptor including, but not limited to, endothelial cells, connective tissue cells, myofibroblasts and glial cells, an isolated polynucleotide sequence encoding the novel growth factor, and compositions useful for diagnostic and/or therapeutic applications.

According to one aspect, the invention provides an isolated and purified nucleic acid molecule which comprises a polynucleotide sequence having at least 85% identity, more preferably at least 90%, and most preferably at least 95% identity to at least nucleotides 1 to 600 of the sequence set out in FIG. 3 (SEQ ID NO:3), at least nucleotides 1 to 966 of the sequence set out in FIG. 5 (SEQ ID NO:5), at least nucleotides 176 to 1285 of the sequence set out in FIG. 7 (SEQ ID NO:7) or at least nucleotides 935 to 1285 set out in FIG. 7 (SEQ ID NO:7). The sequence of at least nucleotides 1 to 600 of the sequence set out in FIG. 3 or at least nucleotides 1 to 966 of the sequence set out in FIG. 5 encodes a 5'-truncated polypeptide, designated PDGF-D (formally designated "VEGF-G"), while at least nucleotides 176 to 1285 of the sequence set out in FIG. 7 (SEQ ID NO:7) encodes a full-length PDGF-D. PDGF-D is structurally homologous to PDGF-A, PDGF-B, VEGF, VEGF-B, VEGF-C and VEGF-D. The sequence of at least nucleotides 935 to 1285 set out in FIG. 7 (SEQ ID NO:7) encodes a portion of the PDGF/VEGF homology domain, which is the bioactive fragment of PDGF-D. This bioactive fragment would also be encoded by the sequence of at least nucleotides 1 to 600 of the sequence set out in FIG. 3 or at least nucleotides 1 to 966 of the sequence set out in FIG. 5. In a preferred embodiment, the nucleic acid molecule is a cDNA which comprises at least nucleotides 1 to 600 of the sequence set out in FIG. 3 (SEQ ID NO:3), at least nucleotides 1 to 966 of the sequence set out in FIG. 5 (SEQ ID NO:5), at least nucleotides 176 to 1285 of the sequence set out in FIG. 7 (SEQ ID NO:7) or at least nucleotides 935 to 1285 set out in FIG. 7 (SEQ ID NO:7). This aspect of the invention also encompasses DNA molecules having a sequence such that they hybridize under stringent conditions with at least nucleotides 1 to 600 of the sequence set out in FIG. 3 (SEQ ID NO:3), at least nucleotides 1 to 966 of the sequence set out in FIG. 5 (SEQ ID NO:5), at least nucleotides 176 to 1285 of the sequence set out in FIG. 7 (SEQ ID NO:7) or at least nucleotides 935 to 1285 set out in FIG. 7 (SEQ ID NO:7) or fragments thereof.

According to a second aspect, the polypeptide of the invention has the ability to stimulate and/or enhance proliferation and/or differentiation and/or growth and/or motility of cells expressing a PDGF-C receptor including, but not limited to, endothelial cells, connective tissue cells, myofibroblasts and glial cells and comprises a sequence of amino acids corresponding to the amino acid sequence set out in FIG. 4 (SEQ ID NO:4) or FIG. 6 (SEQ ID NO:6), or FIG. 8 (SEQ ID NO:8), or a fragment or analog thereof which has the ability to stimulate endothelial cell proliferation, differentiation, migration and/or survival of and/or growth and/or motility of connective tissue cells (such as fibroblasts), myofibroblasts and glial cells. Preferably the polypeptides have at least 85% identity, more preferably at least 90%, and most preferably at least 95% identity to the amino acid sequence of in FIG. 4 (SEQ ID NO:4) or FIG. 6 (SEQ ID NO:6) or FIG. 8 (SEQ ID NO:8), or a fragment or analog thereof having the biological activity of PDGF-D. A preferred fragment is a truncated form of PDGF-D comprising a portion of the PDGF/VEGF homology domain (PVHD) of PDGF-D. The portion of the PVHD is from residues 254–370 of FIG. 8 where the putative proteolytic processing site RKSK starts at amino acid residue 254 (SEQ ID NO:8). However, the PVHD extends toward the N terminus up to residue 234 of FIG. 8 (SEQ ID NO:8). Herein the PVHD is defined as truncated PDGF-D. The truncated PDGF-D is the putative activated form of PDGF-D.

As used in this application, percent sequence identity is determined by using the alignment tool of "MEGALIGN" from the Lasergene package (DNASTAR, Ltd. Abacus House, Manor Road, West Ealing, London W130AS United Kingdom). The MEGALIGN is based on the J. Hein method (Methods in Enzymology, 1990 183 626–645). The PAM 250 residue weight table is used with a gap penalty of eleven and a gap length penalty of three and a K-tuple value of two in the pairwise alignments. The alignment is then refined manually, and the number of identities are estimated in the regions available for a comparison.

Preferably the polypeptide or the encoded polypeptide from a polynucleotide has the ability to stimulate one or more of proliferation, differentiation, motility, survival or vascular permeability of cells expressing a PDGF-D receptor including, but not limited to, vascular endothelial cells, lymphatic endothelial cells, connective tissue cells (such as fibroblasts), myofibroblasts and glial cells. Preferably the polypeptide or the encoded polypeptide from a polynucleotide has the ability to stimulate wound healing. PDGF-D can also have antagonistic effects on cells, but are included in the biological activities of PDGF-D. These abilities are referred to hereinafter as "biological activities of PDGF-D" and can be readily tested by methods known in the art.

As used herein, the term "PDGF-D" collectively refers to the polypeptides of FIG. 4 (SEQ ID NO:4), FIG. 6 (SEQ ID NO:6) or FIG. 8 (SEQ ID NO:8), and fragments or analogs thereof which have the biological activity of PDGF-D as defined above, and to a polynucleotide which can code for PDGF-D, or a fragment or analog thereof having the biological activity of PDGF-D. The polynucleotide can be naked and/or in a vector or liposome.

In another preferred aspect, the invention provides a polypeptide possessing an amino acid sequence:

PXCLLVXRCGGNCXC (SEQ ID NO:25)

which is unique to PDGF-D and differs from the other members of the PDGF/VEGF family of growth factors because of the insertion of the three amino acid residues (NCG) between the third and fourth cysteines (see FIG. 9—SEQ ID NOs:10–18).

Polypeptides comprising conservative substitutions, insertions, or deletions, but which still retain the biological activity of PDGF-D are clearly to be understood to be within the scope of the invention. Persons skilled in the art will be well aware of methods which can readily be used to generate such polypeptides, for example the use of site-directed mutagenesis, or specific enzymatic cleavage and ligation. The skilled person will also be aware that peptidomimetic compounds or compounds in which one or more amino acid residues are replaced by a non-naturally occurring amino acid or an amino acid analog may retain the required aspects of the biological activity of PDGF-D. Such compounds can readily be made and tested for their ability to show the biological activity of PDGF-D by routine activity assay procedures such as the fibroblast proliferation assay and are also within the scope of the invention.

In addition, possible variant forms of the PDGF-D a polypeptide which may result from alternative splicing, as are known to occur with VEGF and VEGF-B, and naturally-occurring allelic variants of the nucleic acid sequence encoding PDGF-D are encompassed within the scope of the invention. Allelic variants are well known in the art, and represent alternative forms or a nucleic acid sequence which comprise substitution, deletion or addition of one or more nucleotides, but which do not result in any substantial functional alteration of the encoded polypeptide.

Such variant forms of PDGF-D can be prepared by targeting non-essential regions of the PDGF-D polypeptide for modification. These non-essential regions are expected to fall outside the strongly-conserved regions indicated in FIG. 9 (SEQ ID NOs:10–18). In particular, the growth factors of the PDGF family, including PDGF-D, are dimeric. PDGF-D differs slightly from VEGF, VEGF-B, VEGF-C, VEGF-D, PlGF, PDGF-A and PDGF-B because it shows complete conservation of only seven of the eight cysteine residues in the PVHD (Olofsson et al., Proc. Natl. Acad. Sci. USA, 1996 93 2576–2581; Joukov et al., EMBO J., 1996 15 290–298). These cysteines are thought to be involved in intra- and inter-molecular disulfide bonding. Loops 1, 2 and 3 of each subunit, which are formed by intra-molecular disulfide bonding, are involved in binding to the receptors for the PDGF/VEGF family of growth factors (Andersson et al., Growth Factors, 1995 12 159–164).

Persons skilled in the art thus are well aware that these cysteine residues should be preserved in any proposed variant form, and that the active sites present in loops 1, 2 and 3 also should be preserved. However, other regions of the molecule can be expected to be of lesser importance for biological function, and therefore offer suitable targets for modification. Modified polypeptides can readily be tested for their ability to show the biological activity of PDGF-D by routine activity assay procedures such as the fibroblast proliferation assay.

It is contemplated that some modified PDGF-D polypeptides will have the ability to bind to PDGF-D receptors on cells including, but not limited to, endothelial cells, connective tissue cells, myofibroblasts and/or glial cells, but will be unable to stimulate cell proliferation, differentiation, migration, motility or survival or to induce vascular proliferation, connective tissue development or wound healing. These modified polypeptides are expected to be able to act as competitive or non-competitive inhibitors of the PDGF-D polypeptides and growth factors of the PDGF/VEGF family, and to be useful in situations where prevention or reduction of the PDGF-D polypeptide or PDGF/VEGF family growth factor action is desirable. Thus such receptor-binding but non-mitogenic, non-differentiation inducing, non-migration inducing, non-motility inducing, non-survival promoting, non-connective tissue promoting, non-wound healing or non-vascular proliferation inducing variants of the PDGF-D polypeptide are also within the scope of the invention, and are referred to herein as "receptor-binding but otherwise inactive variants". Because PDGF-D forms a dimer in order to activate its only known receptor, it is contemplated that one monomer comprises the receptor-binding but otherwise inactive variant modified PDGF-D polypeptide and a second monomer comprises a wild-type PDGF-D or a wild-type growth factor of the PDGF/VEGF family. These dimers can bind to its corresponding receptor but cannot induce downstream signaling.

It is also contemplated that there are other modified PDGF-D polypeptides that can prevent binding of a wild-type PDGF-D or a wild-type growth factor of the PDGF/VEGF family to its corresponding receptor on cells including, but not limited to, endothelial cells, connective tissue cells (such as fibroblasts), myofibroblasts and/or glial cells. Thus these dimers will be unable to stimulate endothelial cell proliferation, differentiation, migration, survival, or induce vascular permeability, and/or stimulate proliferation and/or differentiation and/or motility of connective tissue cells, myofibroblasts or glial cells. These modified polypeptides are expected to be able to act as competitive or non-competitive inhibitors of the PDGF-D growth factor or a growth factor of the PDGF/VEGF family, and to be useful in situations where prevention or reduction of the PDGF-D growth factor or PDGF/VEGF family growth factor action is desirable. Such situations include the tissue remodeling that takes place during invasion of tumor cells into a normal cell population by primary or metastatic tumor formation. Thus such the PDGF-D or PDGF/VEGF family growth factor-binding but non-mitogenic, non-differentiation inducing, non-migration inducing, non-motility inducing, non-survival promoting, non-connective tissue promoting, non-wound healing or non-vascular proliferation inducing variants of the PDGF-D growth factor are also within the scope of the invention, and are referred to herein as "the PDGF-D growth factor-dimer forming but otherwise inactive or interfering variants".

An example of a PDGF-D growth factor-dimer forming but otherwise inactive or interfering variant is where the PDGF-D has a mutation which prevents cleavage of CUB domain from the protein. It is further contemplated that a PDGF-D growth factor-dimer forming but otherwise inactive or interfering variant could be made to comprise a monomer, preferably an activated monomer, of VEGF, VEGF-B, VEGF-C, VEGF-D, PDGF-C, PDGF-A, PDGF-B, PDGF-C, PDGF-D or PlGF linked to a CUB domain that has a mutation which prevents cleavage of CUB domain from the protein. Dimers formed with the above mentioned PDGF-D growth factor-dimer forming but otherwise inactive or interfering variants and the monomers linked to the mutant CUB domain would be unable to bind to their corresponding receptors.

A variation on this contemplation would be to insert a proteolytic site between an activated monomer of VEGF, VEGF-B, VEGF-C, VEGF-D, PDGF-C, PDGF-A, PDGF-B, PDGF-C, PDGF-D or PlGF and the mutant CUB domain linkage which is dimerized to an activated monomer of VEGF, VEGF-B, VEGF-C, VEGF-D, PDGF-A, PDGF-B, PDGF-C, PDGF-D or PlGF. An addition of the specific protease(s) for this proteolytic site would cleave the CUB domain and thereby release an activated dimer that can then bind to its corresponding receptor. In this way, a controlled release of an activated dimer is made possible.

According to a third aspect, the invention provides a purified and isolated nucleic acid encoding a polypeptide or polypeptide fragment of the invention as defined above. The nucleic acid may be DNA, genomic DNA, cDNA or RNA, and may be single-stranded or double stranded. The nucleic acid may be isolated from a cell or tissue source, or of recombinant or synthetic origin. Because of the degeneracy of the genetic code, the person skilled in the art will appreciate that many such coding sequences are possible, where each sequence encodes the amino acid sequence shown in FIG. 4 (SEQ ID NO:4), FIG. 6 (SEQ ID NO:6) or FIG. 8 (SEQ ID NO:8), a bioactive fragment or analog thereof, a receptor-binding but otherwise inactive or partially inactive variant thereof or a PDGF-D dimer-forming but otherwise inactive or interfering variants thereof.

A fourth aspect of the invention provides vectors comprising the cDNA of the invention or a nucleic acid molecule according to the third aspect of the invention, and host cells transformed or transfected with nucleic acids molecules or vectors of the invention. These may be eukaryotic or prokaryotic in origin. These cells are particularly suitable for expression of the polypeptide of the invention, and include insect cells such as Sf9 cells, obtainable from the American Type Culture Collection (ATCC SRL-171), transformed with a baculovirus vector, and the human embryo kidney cell line 293—EBNA transfected by a suitable expression plasmid. Preferred vectors of the invention are expression vectors in which a nucleic acid according to the invention is operatively connected to one or more appropriate promoters and/or other control sequences, such that appropriate host cells transformed or transfected with the vectors are capable of expressing the polypeptide of the invention. Other preferred vectors are those suitable for transfection of mammalian cells, or for gene therapy, such as adenoviral-, vaccinia- or retroviral-based vectors or liposomes. A variety of such vectors is known in the art.

The invention also provides a method of making a vector capable of expressing a polypeptide encoded by a nucleic acid molecule according to the invention, comprising the steps of operatively connecting the nucleic acid molecule to one or more appropriate promoters and/or other control sequences, as described above.

The invention further provides a method of making a polypeptide according to the invention, comprising the steps of expressing a nucleic acid or vector of the invention in a host cell, and isolating the polypeptide from the host cell or from the host cell's growth medium.

In yet a further aspect, the invention provides an antibody specifically reactive with a polypeptide of the invention or a fragment of the polypeptide. This aspect of the invention includes antibodies specific for the variant forms, immunoreactive fragments, analogs and recombinants of PDGF-D. Such antibodies are useful as inhibitors or agonists of PDGF-D and as diagnostic agents for detecting and quantifying PDGF-D. Polyclonal or monoclonal antibodies may be used. Monoclonal and polyclonal antibodies can be raised against polypeptides of the invention or fragment or analog thereof using standard methods in the art. In addition the polypeptide can be linked to an epitope tag, such as the FLAG® octapeptide (Sigma, St. Louis, Mo.), to assist in affinity purification. For some purposes, for example where a monoclonal antibody is to be used to inhibit effects of PDGF-D in a clinical situation, it may be desirable to use humanized or chimeric monoclonal antibodies. Such antibodies may be further modified by addition of cytotoxic or cytostatic drug(s). Methods for producing these, including recombinant DNA methods, are also well known in the art.

This aspect of the invention also includes an antibody which recognizes PDGF-D and is suitably labeled.

Polypeptides or antibodies according to the invention may be labeled with a detectable label, and utilized for diagnostic purposes. Similarly, the thus-labeled polypeptide of the invention may be used to identify its corresponding receptor in situ. The polypeptide or antibody may be covalently or non-covalently coupled to a suitable supermagnetic, paramagnetic, electron dense, ecogenic or radioactive agent for imaging. For use in diagnostic assays, radioactive or non-radioactive labels may be used. Examples of radioactive labels include a radioactive atom or group, such as $^{125}$I or $^{32}$P. Examples of non-radioactive labels include enzymatic labels, such as horseradish peroxidase or fluorimetric labels, such as fluorescein-5-isothiocyanate (FITC). Labeling may be direct or indirect, covalent or non-covalent.

Clinical applications of the invention include diagnostic applications, acceleration of angiogenesis in tissue or organ transplantation, or stimulation of wound healing, or connective tissue development, or to establish collateral circulation in tissue infarction or arterial stenosis, such as coronary artery disease, and inhibition of angiogenesis in the treatment of cancer or of diabetic retinopathy and inhibition of tissue remodeling that takes place during invasion of tumor cells into a normal cell population by primary or metastatic tumor formation. Quantitation of PDGF-D in cancer biopsy specimens may be useful as an indicator of future metastatic risk.

PDGF-D may also be relevant to a variety of lung conditions. PDGF-D assays could be used in the diagnosis of various lung disorders. PDGF-D could also be used in the treatment of lung disorders to improve blood circulation in the lung and/or gaseous exchange between the lungs and the blood stream. Similarly, PDGF-D could be used to improve blood circulation to the heart and $O_2$ gas permeability in cases of cardiac insufficiency. In a like manner, PDGF-D could be used to improve blood flow and gaseous exchange in chronic obstructive airway diseases.

Thus the invention provides a method of stimulation of angiogenesis, lymphangiogenesis, neovascularization, connective tissue development and/or wound healing in a mammal in need of such treatment, comprising the step of administering an effective dose of PDGF-D, or a fragment or an analog thereof which has the biological activity of PDGF-D to the mammal. Optionally the PDGF-D, or fragment or analog thereof may be administered together with, or in conjunction with, one or more of VEGF, VEGF-B, VEGF-C, VEGF-D, PlGF, PDGF-A, PDGF-B, PDGF-C, FGF and/or heparin.

Conversely, PDGF-D antagonists (e.g. antibodies and/or competitive or noncompetitive inhibitors of binding of PDGF-D in both dimer formation and receptor binding) could be used to treat conditions, such as congestive heart failure, involving accumulation of fluid in, for example, the lung resulting from increases in vascular permeability, by exerting an offsetting effect on vascular permeability in order to counteract the fluid accumulation. Administrations of PDGF-D could be used to treat malabsorptive syndromes in the intestinal tract, liver or kidneys as a result of its blood circulation increasing and vascular permeability increasing activities.

Thus, the invention provides a method of inhibiting angiogenesis, lymphangiogenesis, neovascularization, connective tissue development and/or wound healing in a mammal in need of such treatment, comprising the step of administering an effective amount of an antagonist of PDGF-D to the mammal. The antagonist may be any agent that prevents the action of PDGF-D, either by preventing the binding of PDGF-D to its corresponding receptor on the target cell, or by preventing activation of the receptor, such as using receptor-binding PDGF-D variants. Suitable antagonists include, but are not limited to, antibodies directed against PDGF-D; competitive or non-competitive inhibitors of binding of PDGF-D to the PDGF-D receptor(s), such as the receptor-binding or PDGF-D dimer-forming but non-mitogenic PDGF-D variants referred to above; and anti-sense nucleotide sequences as described below.

A method is provided for determining agents that bind to an activated truncated form of PDGF-D. The method comprises contacting an activated truncated form of PDGF-D with a test agent and monitoring binding by any suitable means. Agents can include both compounds and other proteins.

The invention provides a screening system for discovering agents that bind an activated truncated form of PDGF-D. The screening system comprises preparing an activated truncated form of PDGF-D, exposing the activated truncated form of PDGF-D to a test agent, and quantifying the binding of said agent to the activated truncated form of PDGF-D by any suitable means. This screening system can also be used to identify agents which inhibit the proteolytic cleavage of the full length PDGF-D protein and thereby prevent the release of the activated truncated form of PDGF-D. For this use, the full length PDGF-D must be prepared.

Use of this screen system provides a means to determine compounds that may alter the biological function of PDGF-D. This screening method may be adapted to large-scale, automated procedures such as a PANDEX® (Baxter-Dade Diagnostics) system, allowing for efficient high-volume screening of potential therapeutic agents.

For this screening system, an activated truncated form of PDGF-D or full length PDGF-D is prepared as described herein, preferably using recombinant DNA technology. A test agent, e.g. a compound or protein, is introduced into a reaction vessel containing the activated truncated form of or full length PDGF-D. Binding of the test agent to the activated truncated form of or full length PDGF-D is determined by any suitable means which include, but is not limited to, radioactively- or chemically-labeling the test agent. Binding of the activated truncated form of or full length PDGF-D may also be carried out by a method disclosed in U.S. Pat. No. 5,585,277, which is incorporated by reference. In this method, binding of the test agent to the activated truncated form of or full length PDGF-D is assessed by monitoring the ratio of folded protein to unfolded protein. Examples of this monitoring can include, but are not limited to, monitoring the sensitivity of the activated truncated form of or full length PDGF-D to a protease, or amenability to binding of the protein by a specific antibody against the folded state of the protein.

Those of skill in the art will recognize that $IC_{50}$ values are dependent on the selectivity of the agent tested. For example, an agent with an $IC_{50}$ which is less than 10 nM is generally considered an excellent candidate for drug therapy. However, an agent which has a lower affinity, but is selective for a particular target, may be an even better candidate. Those skilled in the art will recognize that any information regarding the binding potential, inhibitory activity or selectivity of a particular agent is useful toward the development of pharmaceutical products.

Where PDGF-D or a PDGF-D antagonist is to be used for therapeutic purposes, the dose(s) and route of administration will depend upon the nature of the patient and condition to be treated, and will be at the discretion of the attending physician or veterinarian. Suitable routes include oral, subcutaneous, intramuscular, intraperitoneal or intravenous injection, parenteral, topical application, implants etc. Topical application of PDGF-D may be used in a manner analogous to VEGF. Where used for wound healing or other use in which enhanced angiogenesis is advantageous, an effective amount of the truncated active form of PDGF-D is administered to an organism in need thereof in a dose between about 0.1 and 1000 µg/kg body weight.

The PDGF-D or a PDGF-D antagonist may be employed in combination with a suitable pharmaceutical carrier. The resulting compositions comprise a therapeutically effective amount of PDGF-D or a PDGF-D antagonist, and a pharmaceutically acceptable non-toxic salt thereof, and a pharmaceutically acceptable solid or liquid carrier or adjuvant. Examples of such a carrier or adjuvant include, but are not limited to, saline, buffered saline, Ringer's solution, mineral oil, talc, corn starch, gelatin, lactose, sucrose, microcrystalline cellulose, kaolin, mannitol, dicalcium phosphate, sodium chloride, alginic acid, dextrose, water, glycerol, ethanol, thickeners, stabilizers, suspending agents and combinations thereof. Such compositions may be in the form of solutions, suspensions, tablets, capsules, creams, salves, elixirs, syrups, wafers, ointments or other conventional forms. The formulation to suit the mode of administration. Compositions which comprise PDGF-D may optionally further comprise one or more of PDGF-A, PDGF-B, PDGF-C, VEGF, VEGF-B, VEGF-C, VEGF-D, PlGF and/or heparin. Compositions comprising PDGF-D will contain from about 0.1% to 90% by weight of the active compound(s), and most generally from about 10% to 30%.

For intramuscular preparations, a sterile formulation, preferably a suitable soluble salt form of the truncated active form of PDGF-D, such as hydrochloride salt, can be dissolved and administered in a pharmaceutical diluent such as pyrogen-free water (distilled), physiological saline or 5% glucose solution. A suitable insoluble form of the compound may be prepared and administered as a suspension in an aqueous base or a pharmaceutically acceptable oil base, e.g. an ester of a long chain fatty acid such as ethyl oleate.

According to yet a further aspect, the invention provides diagnostic/prognostic devices typically in the form of test kits. For example, in one embodiment of the invention there is provided a diagnostic/prognostic test kit comprising an antibody to PDGF-D and a means for detecting, and more preferably evaluating, binding between the antibody and PDGF-D. In one preferred embodiment of the diagnostic/ prognostic device according to the invention, a second antibody (the secondary antibody) directed against antibodies of the same isotype and animal source of the antibody directed against PDGF-D (the primary antibody) is provided. The secondary antibody is coupled directly or indirectly to a detectable label, and then either an unlabeled primary antibody or PDGF-D is substrate-bound so that the PDGF-D/primary antibody interaction can be established by determining the amount of label bound to the substrate following binding between the primary antibody and PDGF-D and the subsequent binding of the labeled secondary antibody to the primary antibody. In a particularly preferred embodiment of the invention, the diagnostic/ prognostic device may be provided as a conventional enzyme-linked immunosorbent assay (ELISA) kit.

In another alternative embodiment, a diagnostic/ prognostic device may comprise polymerase chain reaction means for establishing sequence differences of a PDGF-D of a test individual and comparing this sequence structure with that disclosed in this application in order to detect any abnormalities, with a view to establishing whether any aberrations in PDGF-D expression are related to a given disease condition.

In addition, a diagnostic/prognostic device may comprise a restriction length polymorphism (RFLP) generating means utilizing restriction enzymes and genomic DNA from a test individual to generate a pattern of DNA bands on a gel and comparing this pattern with that disclosed in this application in order to detect any abnormalities, with a view to establishing whether any aberrations in PDGF-D expression are related to a given disease condition.

In accordance with a further aspect, the invention relates to a method of detecting aberrations in PDGF-D gene structure in a test subject which may be associated with a disease condition in the test subject. This method comprises providing a DNA sample from said test subject; contacting the DNA sample with a set of primers specific to PDGF-D DNA operatively coupled to a polymerase and selectively amplifying PDGF-D DNA from the sample by polymerase chain reaction, and comparing the nucleotide sequence of the amplified PDGF-D DNA from the sample with the nucleotide sequences shown in FIG. 3 (SEQ ID NO:3), FIG. 5 (SEQ ID NO:5) or FIG. 7 (SEQ ID NO:7). The invention also includes the provision of a test kit comprising a pair of primers specific to PDGF-D DNA operatively coupled to a polymerase, whereby said polymerase is enabled to selectively amplify PDGF-D DNA from a DNA sample.

The invention also provides a method of detecting PDGF-D in a biological sample, comprising the step of contacting the sample with a reagent capable of binding PDGF-D, and detecting the binding. Preferably the reagent capable of binding PDGF-D is an antibody directed against PDGF-D, particularly a monoclonal antibody. In a preferred embodiment the binding and/or extent of binding is detected by means of a detectable label; suitable labels are discussed above.

In another aspect, the invention relates to a protein dimer comprising the PDGF-D polypeptide, particularly a disulfide-linked dimer. The protein dimers of the invention include both homodimers of PDGF-D polypeptide and heterodimers of PDGF-D and VEGF, VEGF-B, VEGF-C, VEGF-D, PlGF, PDGF-A, PDGF-B or PDGF-C.

According to a yet further aspect of the invention there is provided a method for isolation of PDGF-D comprising the step of exposing a cell which expresses PDGF-D to heparin to facilitate release of PDGF-D from the cell, and purifying the thus-released PDGF-D.

Another aspect of the invention involves providing a vector comprising an anti-sense nucleotide sequence which is complementary to at least a part of a DNA sequence which encodes PDGF-D or a fragment or analog thereof that has the biological activity of PDGF-D. In addition the anti-sense nucleotide sequence can be to the promoter region of the PDGF-D gene or other non-coding region of the gene which may be used to inhibit, or at least mitigate, PDGF-D expression.

According to a yet further aspect of the invention such a vector comprising an anti-sense sequence may be used to inhibit, or at least mitigate, PDGF-D expression. The use of a vector of this type to inhibit PDGF-D expression is favored in instances where PDGF-D expression is associated with a disease, for example where tumors produce PDGF-D in order to provide for angiogenesis, or tissue remodeling that takes place during invasion of tumor cells into a normal cell population by primary or metastatic tumor formation. Transformation of such tumor cells with a vector containing an anti-sense nucleotide sequence would suppress or retard angiogenesis, and so would inhibit or retard growth of the tumor or tissue remodeling.

Another aspect of the invention relates to the discovery that the full length PDGF-D protein is likely to be a latent growth factor that needs to be activated by proteolytic processing to release an active PDGF/VEGF homology domain. A putative proteolytic site is found in residues 255–258 in the full length protein, residues -RKSK-(SEQ ID NO:9). This is a dibasic motif. The -RKSK-(SEQ ID NO:9) putative proteolytic site is also found in PDGF-A, PDGF-B, VEGF-C and VEGF-D. In these four proteins, the putative proteolytic site is also found just before the minimal domain for the PDGF/VEGF homology domain. Together these facts indicate that this is the proteolytic site.

Preferred proteases include, but are not limited, to plasmin, Factor X and enterokinase. The N-terminal CUB domain may function as an inhibitory domain which might be used to keep PDGF-D in a latent form in some extracellular compartment and which is removed by limited proteolysis when PDGF-D is needed.

According to this aspect of the invention, a method is provided for producing an activated truncated form of PDGF-D or for regulating receptor-binding specificity of PDGF-D. These methods comprise the steps of expressing an expression vector comprising a polynucleotide encoding a polypeptide having the biological activity of PDGF-D and supplying a proteolytic amount of at least one enzyme for processing the expressed polypeptide to generate the activated truncated form of PDGF-D.

This aspect also includes a method for selectively activating a polypeptide having a growth factor activity. This method comprises the step expressing an expression vector comprising a polynucleotide encoding a polypeptide having a growth factor activity, a CUB domain and a proteolytic site between the polypeptide and the CUB domain, and supplying a proteolytic amount of at least one enzyme for processing the expressed polypeptide to generate the activated polypeptide having a growth factor activity.

In addition, this aspect includes the isolation of a nucleic acid molecule which codes for a polypeptide having the biological activity of PDGF-D and a polypeptide thereof which comprises a proteolytic site having the amino acid sequence RKSR (SEQ ID NO:9) or a structurally conserved amino acid sequence thereof.

Also this aspect includes an isolated dimer comprising an activated monomer of PDGF-D and an activated monomer of VEGF, VEGF-B, VEGF-C, VEGF-D, PDGF-D, PDGF-A, PDGF-B, PDGF-C or PlGF linked to a CUB domain, or alternatively, an activated monomer of VEGF, VEGF-B, VEGF-C, VEGF-D, PDGF-D, PDGF-A, PDGF-B or PlGF and an activated monomer of PDGF-D linked to a CUB domain. The isolated dimer may or may not include a proteolytic site between the activator monomer and the CUB domain linkage.

Polynucleotides of the invention such as those described above, fragments of those polynucleotides, and variants of those polynucleotides with sufficient similarity to the non-coding strand of those polynucleotides to hybridize thereto under stringent conditions all are useful for identifying, purifying, and isolating polynucleotides encoding other, non-human, mammalian forms of PDGF-D. Thus, such polynucleotide fragments and variants are intended as aspects of the invention. Exemplary stringent hybridization conditions are as follows: hybridization at 42° C. in 5×SSC, 20 mM NaPO$_4$, pH 6.8, 50% formamide; and washing at 42° C. in 0.2×SSC. Those skilled in the art understand that it is desirable to vary these conditions empirically based on the length and the GC nucleotide base content of the sequences to be hybridized, and that formulas for determining such variation exist. See for example Sambrook et al, "Molecular Cloning: A Laboratory Manual", Second Edition, pages 9.47–9.51, Cold Spring Harbor, N.Y.: Cold Spring Harbor Laboratory (1989).

Moreover, purified and isolated polynucleotides encoding other, non-human, mammalian PDGF-D forms also are aspects of the invention, as are the polypeptides encoded thereby and 30 antibodies that are specifically immunoreactive with the non-human PDGF-D variants. Thus, the invention includes a purified and isolated mammalian PDGF-D polypeptide and also a purified and isolated polynucleotide encoding such a polypeptide.

It will be clearly understood that nucleic acids and polypeptides of the invention may be prepared by synthetic means or by recombinant means, or may be purified from natural sources.

It will be clearly understood that for the purposes of this specification the word "comprising" means "included but not limited to". The corresponding meaning applies to the word "comprises".

BRIEF DESCRIPTION OF THE DRAWINGS

FIG. 1 (SEQ ID NO:1) shows a nucleotide sequence that includes a cDNA sequence encoding the C-terminal part of human PDGF-D (hPDGF-D). The nucleotides which encode for the partial fragment of hPDGF-D are 1 to 198. The deduced partial amino acid sequence of hPDGF-D (66 amino acid residues-SEQ ID NO:2) derived from nucleotides 1 to 198 of FIG. 1 is shown in FIG. 2;

FIG. 3 (SEQ ID NO:3) shows an extended sequence of a partial human cDNA encoding for the hPDGF-D. The translated cDNA sequence is from nucleotide 1 to 600. The deduced partial amino acid sequence of hPDGF-D (200 residues-SEQ ID NO:4) derived from nucleotides 1 to 600 of FIG. 3 is shown in FIG. 4;

FIG. 5 shows a still further extended nucleotide sequence of a partial human cDNA. The nucleotides which encode for the 5'-truncated full-length hPDGF-D are 1 to 966 (SEQ ID NO:5). The deduced partial amino acid sequence of hPDGF-D (322 residues-SEQ ID NO:6) derived from nucleotides 1 to 966 of FIG. 5 is shown in FIG. 6;

FIG. 7 (SEQ ID NO:7) shows the complete nucleotide sequence of cDNA encoding a hPDGF-D(1116 bp) and the deduced amino acid sequence of full-length hPDGF-D encoded thereby which consists of 370 amino acid residues (FIG. 8-SEQ ID NO:8);

FIG. 9 shows an amino acid sequence alignment of the PDGF/VEGF-homology domain in hPDGF-D with several growth factors belonging to the VEGF/PDGF family (SEQ ID NOs:10–18, respectively);

FIG. 11 provides the amino acid sequence alignment of the CUB domain present in hPDGF-D (SEQ ID NO:19) and other CUB domains present in human bone morphogenic protein-1 (hBMP-1, 3 CUB domains CUB1–3) (SEQ ID NOs:20–22, respectively) and in human neuropilin-1 (2 CUB domains) (SEQ ID NOs:23–24, respectively);

DETAILED DESCRIPTION OF PREFERRED EMBODIMENTS

Figure 10:
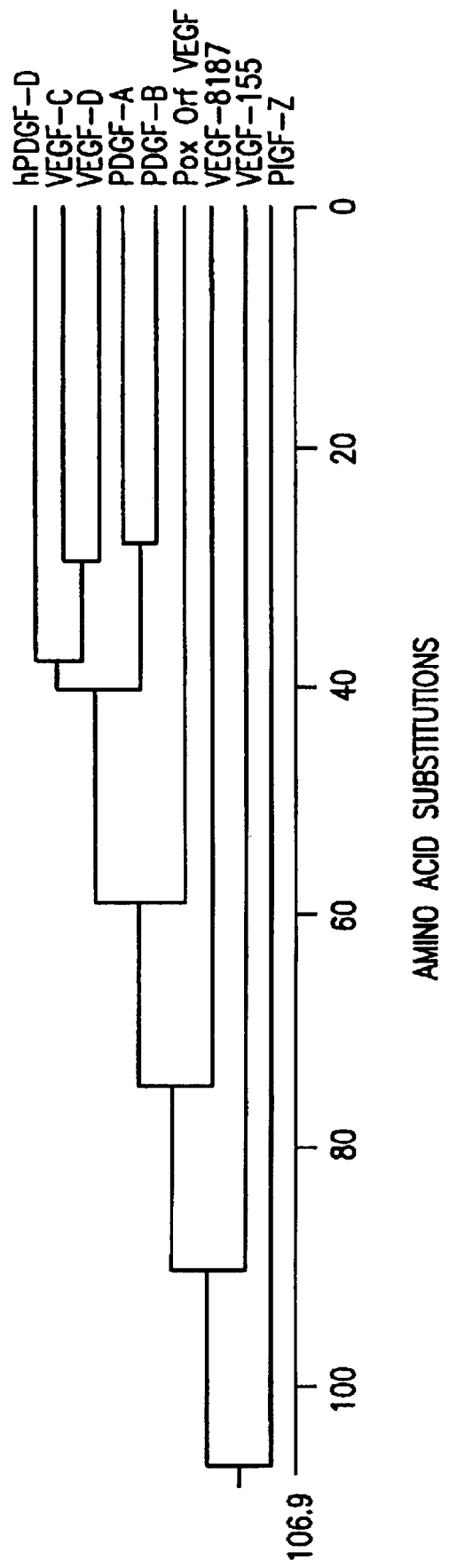
FIG. 10 shows a phylogenetic tree of several growth factors belonging to the VEGF/PDGF family.

FIG. 1 shows a nucleotide sequence of human cDNA which encodes a C-terminal portion of a novel growth factor, referred to herein as PDGF-D (formerly VEGF-G). PDGF-D is a new member of the VEGF/PDGF family. The nucleotide sequence of FIG. 1 (SEQ ID NO:1) was derived from a human EST sequence (id. AI488780) in the dbEST database at the NCBI in Washington, DC. The nucleotides 1 to 198 of the cDNA of FIG. 1 (SEQ ID NO:1) encodes a 66 amino acid polypeptide (FIG. 2—SEQ ID NO:2) which shows some sequence similarity to the known members of the VEGF/PDGF family.

The amino acid sequence of the polypeptide encoded by the nucleotides 1 to 198 of the polynucleotide of FIG. 1 (SEQ ID NO:1) is shown in FIG. 2 (SEQ ID NO:2).

To generate more sequence information on human PDGF-D, a human fetal lung λgt10 cDNA library was screened using a 327 bp polymerase chain reaction (PCR)-generated probe, based on the originally identified EST sequence. The probe was generated from DNA from a commercially available human fetal lung cDNA library (Clontech) which was amplified by PCR using two primers derived from the identified EST (AI488780). The primers were:

5'-GTCGTGGAACTGTCAACTGG (forward) (SEQ ID NO:26) and

5'-CTCAGCAACCACTTGTGTTC (reverse) (SEQ ID NO:27).

The amplified 327 bp fragment was cloned into the pCR2.1 vector (Invitrogen). Nucleotide sequencing verified that the insert corresponded to the EST. The screen identified several positive clones. The inserts from two of these clones, clones 5 and 8 were subcloned into pBluescript and subjected to nucleotide sequencing using internal or vector-specific primers. The nucleotide sequences determined were identical in both clones and are shown in FIG. 3 (SEQ ID NO:3). The coding region of the 690 bp polynucleotide is nucleotides 1–600 (SEQ ID NO:3) that encodes for a large portion of hPDGF-D with the exception of the 5'-end. This portion of hPDGF-D includes the bioactive fragment of hPDGF-D. The deduced partial amino acid sequence of hPDGF-D (200 residues-SEQ. ID NO:4) derived from nucleotides 1 to 600 of FIG. 3 (SEQ ID NO:3) is shown in FIG. 4 (SEQ ID NO:4).

Extended nucleotide sequencing of the isolated human PDGF-D cDNA clones from this human fetal lung cDNA library has provided additional sequence. FIG. 5 (SEQ ID NO:5) shows a nucleotide sequence of a partial human cDNA (1934 bp) that encodes hPDGF-D. The coding region of the 1934 bp polynucleotide is nucleotides 1 to 966 that encodes for hPDGF-D except for the most 5'-end of the polypeptide. The deduced partial amino acid sequence of hPDGF-D (322 residues-SEQ ID NO:6) derived from nucleotides 1 to 966 of FIG. 5 (SEQ ID NO:5) is shown in FIG. 6 (SEQ ID NO:6).

FIG. 7 (SEQ ID NO:7) shows a polynucleotide sequence of cDNA encoding a full-length hPDGF-D. The region encoding PDGF-D is 1116 bp. The deduced amino acid sequence of full-length hPDGF-D is 370 amino acid residues (FIG. 8-SEQ ID NO:8).

The sequence for the 5' end of full-length PDGF-D was obtained using Rapid Amplification of cDNA Ends (RACE) PCR, and clones containing cDNA from the human heart (Marathon-Ready™ cDNA, Clontech, Cat# 7404-1). These cDNA clones have an adaptor sequence attached to the 5' end of each clone, including a site for primer called Adaptor Primer 1 (Clontech: 5'9 CCATCCTAATACGACTCACTAT-AGGGC 3'9) (SEQ ID NO:28). This primer and a second primer 5'AGTGGGATCCGTTACTGA TGGAGAGTTAT 3' (SEQ ID NO:29) were used to amplify the sequence found at the 5' end of PDGF-D. In the PCR reaction a special polymerase mix was used (Advantage<<-GC cDNA PCR Kit, Clontech, Cat# K1907-1). The reaction mix included (in microliters):

| | |
|---|---|
| Adaptor Primer 1 | 1 |
| Gene specific primer | 1 |
| Template (Human Heart cDNA) | 5 |
| GC-Melt (from the K1907-1 Kit) | 5 |
| 5xGC cDNA PCR Reaction Buffer | 10 |
| 50x dNTP mix | 1 |
| Sterile H2O | 27 |
| Total | 50 |

The 5' end of PDGF-D was amplified for 31 cycles, five cycles consisted of 45 seconds denaturation at 94° C. and four minutes extension at 72° C., five cycles consisted of 45 seconds denaturation at 94° C. and four minutes extension at 70° C., and five cycles consisted of 45 seconds denaturation at 94° C. and four minutes extension at 68° C. and an initial denaturation step at 94° C. for two minutes. From this PCR, an approximately 790 bp long product was obtained. This product was run on a 1% agarose gel, purified (QIAquick gel extraction Kit, Qiagen, Cat # 28706) from the gel, cloned into a vector (TOPO TA Cloning Kit, Invitrogen) and transformed into bacteria (E.Coli). Transformed bacteria were plated, and incubated at 37° C. overnight. Single colonies were picked and grown in fresh media overnight. Plasmids were prepared (QIAprep Spin Miniprep Kit, Qiagen, Cat# 27106) and sequenced with the plasmid primers, T7 and M13R. The result of this sequencing was that 312 bp of previously unknown PDGF-D sequence was obtained. The rest of the sequence (478 bp) was identical with previously obtained sequence from other PDGF-D cDNA clones.

Figure 9B:
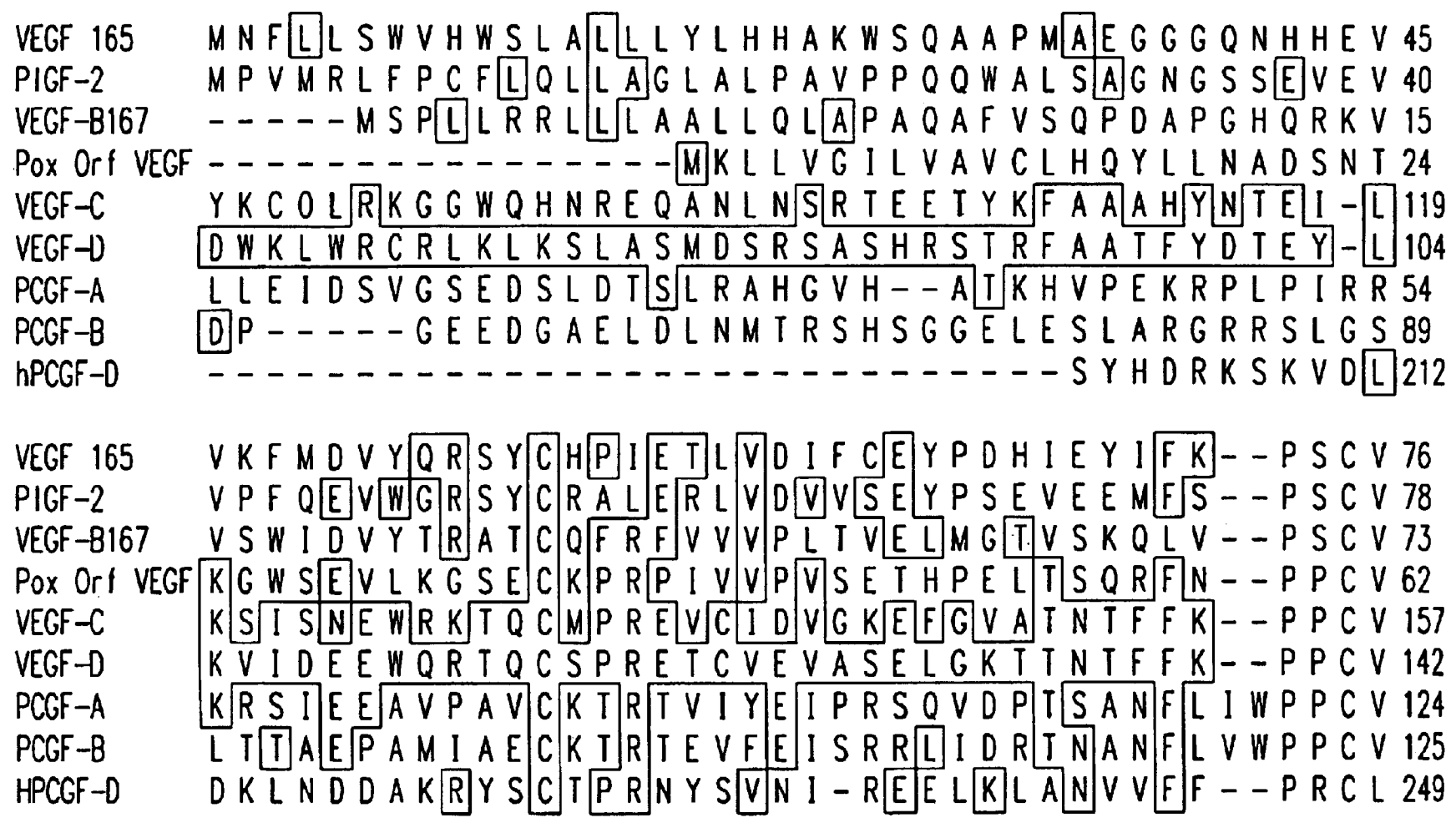
Figure 9C:
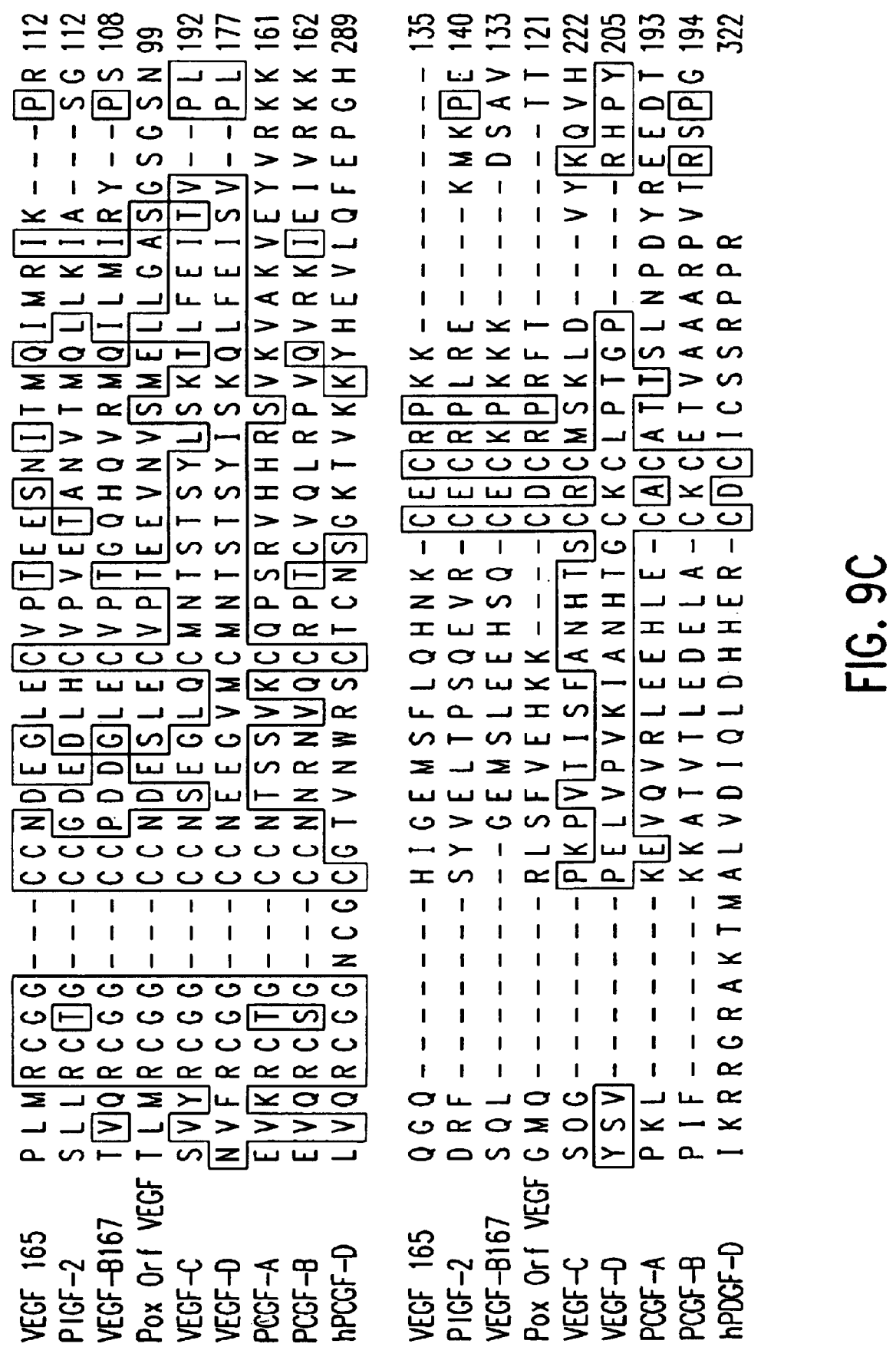

FIG. 9 shows the amino acid sequence alignment of the PDGF/VEGF-homology domain of PDGF-D (found in the C-terminal region of the polypeptide) with the PDGF/VEGF-homology domains of PDGF/VEGF family members, VEGF$_{165}$, PlGF-2, VEGF-B$_{167}$, Pox Orf VEGF, VEGF-C, VEGF-D, PDGF-A and PDGF-B (SEQ ID NOs:10–18, respectively). Some of the amino acid sequences in the N- and C-terminal regions in VEGF-C and VEGF-D have been deleted in this figure. Gaps were introduced to optimize the alignment. This alignment was generated using the MEGALIGN alignment tool based on the method of J. Hein, (Methods Enzymol. 1990 183 626–45) The PAM 250 residue weight table is used with a gap penalty of eleven and a gap length penalty of three and a K-tuple value of two in the pairwise alignments. The alignment is then refined manually, and the number of identities are estimated in the regions available for a comparison. The boxed residues indicate amino acids which match the VEGF-D within two distance units.

The alignment shows that PDGF-D has the expected pattern of invariant cysteine residues, a hallmark of members of this family, with two exceptions. The first exception occurs between cysteine 3 and 4. Normally these two cysteines are spaced by 2 residues and with PDGF-D there is an insertion of three extra amino acids (NCA). This feature of the sequence in PDGF-D was highly unexpected. The second is that the invariant fifth cysteine found in the other members of the PDGF/VEGF family is not conserved in PDGF-D. This feature is unique to PDGF-D.

Based on the amino acid sequence alignments in FIG. 9, a phylogenetic tree was constructed and is shown in FIG. 10. The data show that the PVHD of PDGF-D is closely related to the PVHDs of VEGF-C and VEGF-D.

CUB Domain

Figure 11:
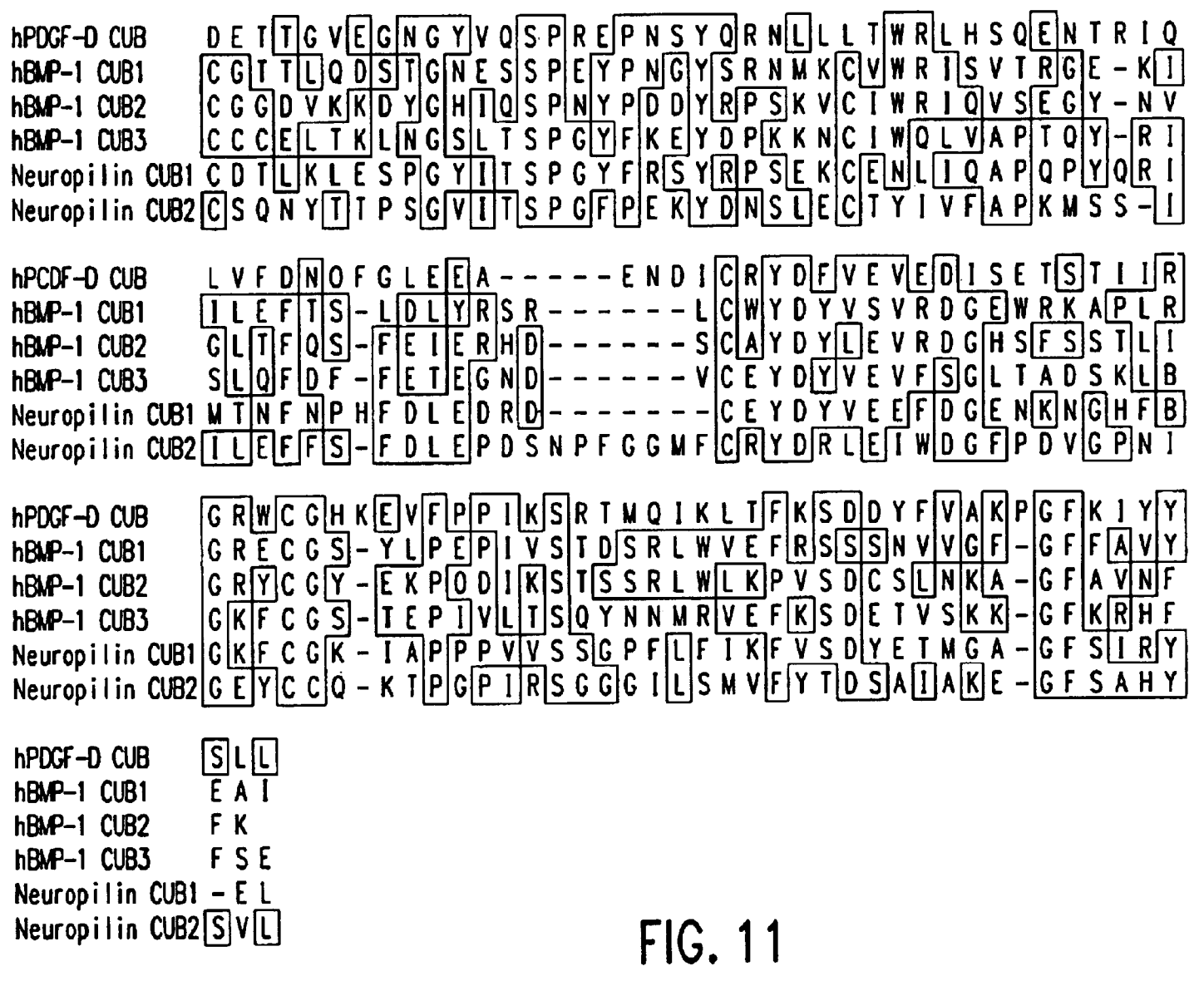

The N-terminal region of the partial PDGF-D amino acid sequence of FIG. 11 (residues 53–170) (SEQ ID NO:8) has second distinct protein domain which is referred to as a CUB domain (Bork and Beckmann, J. Mol. Biol., 1993 231, 539–545). This domain of about 115 amino acids was originally identified in complement factors C1r/C1s, but has recently been identified in several other extracellular proteins including signaling molecules such as bone morphogenic protein 1 (BMP-1) (Wozney et al.,Science, 1988 242, 1528–1534) as well as in several receptor molecules such as neuropilin-1 (NP-1) (Soker et al., Cell, 1998 92 735–745). The functional roles of CUB domains are not clear but they may participate in protein-protein interactions or in interactions with carbohydrates including heparin sulfate proteoglycans. These interactions may play a role the proteolytic activation of PDGF-D.

As shown in FIG. 11, the amino acid sequences from several CUB-containing proteins were aligned. The results show that the single CUB domain in human PDGF-D (SEQ ID NO:19) displays a significant identify with the most closely related CUB domains. Sequences from human BMP-1, with 3 CUB domains (CUBs1–3) (SEQ ID NOs:20–22, respectively) and human neuropilin-1 with 2 CUB domains (CUBs1–2) (SEQ ID NOs:23–24, respectively) are shown. This alignment was generated as described above.

EXAMPLE 1

Expression of PDGF-D Transcripts

To investigate the tissue expression of PDGF-D in several human tissues, a Northern blot was done using a commercial Multiple Tissue Northern blot (MTN, Clontech). The blots were hybridized at according to the instructions from the supplier using ExpressHyb solution at 68° C. for one hour (high stringency conditions), and probed with the 327 bp PCR-generated probe from the human fetal lung cDNA library (see description above). The blots were subsequently washed at 50° C. in 2×SSC with 0.05% SDS for 30 minutes and at 50° C. in 0.1×SSC with 0.1% SDS for an additional 40 minutes. The blots were then put on film and exposed at −70° C. The results, summarized in Table 1, showed that expression of PDGF-D transcripts were most abundant in heart, pancreas and ovary while lower expression levels were seen in placenta, liver, kidney, prostate and testis. The human PDGF-D transcript was around 4 kb in length.

TABLE 1

Relative expression levels of PDGF-D transcripts in several human tissues as determined by Northern blot analysis

| Tissue level* | Expression |
|---|---|
| Heart | +++++ |
| Brain | n.d. |
| Placenta | ++ |
| Lung | + |
| Liver | ++ |
| Skeletal muscle | n.d. |
| Kidney | ++ |
| Pancreas | ++++ |
| Spleen | + |
| Thymus | + |
| Prostate | ++ |
| Testis | +++ |
| Ovary | +++++ |
| Small intestine | ++ |
| Colon | + |
| Peripheral blood leucocytes | + |

*The relative intensities of the bands were visually determined (+++++) highest expression and (+) lowest expression; n.d. not detected

EXAMPLE 2

Receptor Binding Properties of a Truncated PDGF-D

To assess the interactions between a truncated PDGF-D and the VEGF receptors, truncated PDGF-D was tested for its capacity to bind to soluble Ig-fusion proteins containing the extracellular domains of human VEGFR-1, VEGFR-2 and VEGFR-3 (Olofsson et al., Proc. Natl. Acad. Sci. USA, 1998 95 11709–11714). An expression vector encoding the PDGF/VEGF homology domain of PDGF-D was generated in the vector pSecTag (Invitrogen). The primers 5'-CCCAAGCTTGAAGATCTTGAGAATAT 3' (forward) (SEQ ID NO:30) and 5'-TGCTCTAGATCGAGGTG-GTCTT 3' (reverse) (SEQ ID NO:31) were used to amplify a 429 bp fragment (nucleotides 556 to 966 in FIG. 5) (SEQ ID NO:5) encoding amino acid residues 186 to 322 of FIG. 6 (SEQ ID NO:6) or 234 to 370 of FIG. 8 (SEQ ID NO:8), which are identical. The fragment was subsequently cloned into a HindIII and XbaI digested expression vector. COS cells were transfected with the expression vector encoding truncated PDGF-D or a control vector using calcium phosphate precipitation. The expressed polypeptide included a C-terminal c-myc tag and a 6X His tag (both derived from the pSecTag vector.

The Ig-fusion proteins, designated VEGFR-1-Ig, VEGFR-2-Ig and VEGFR-3-Ig, were transiently expressed in human 293 EBNA cells. All Ig-fusion proteins were human VEGFRs. Cells were incubated for 24 hours after transfection, washed with Dulbecco's Modified Eagle Medium (DMEM) containing 0.2% bovine serum albumin (BSA) and starved for 24 hours. The fusion proteins were then precipitated from the clarified conditioned medium using protein A-Sepharose beads (Pharmacia). The beads were combined with 100 microliters of lOX binding buffer (5% BSA, 0.2% Tween 20 and 10 μg/ml heparin) and 900 microliter of conditioned medium prepared from the COS cells transfected with the expression vector for truncated PDGF-D or the control vector. The cells were then metabolically labeled with $^{35}$S-cysteine and methionine (Promix, Amersham) for 4 to 6 hours. After 2.5 hours, at room temperature, the Sepharose beads were washed 3 times with binding buffer at 4° C., once with phosphate buffered saline (PBS) and boiled in SDS-PAGE buffer. Labeled proteins that were bound to the Ig-fusion proteins were analyzed by SDS-PAGE under reducing conditions. Radiolabeled proteins were detected using a phosphorimager analyzer and/or on film. In all these analyses, radiolabeled PDGF-D failed to show any interaction with any of the VEGF receptors. These results indicate that secreted truncated PDGF-D does not bind to VEGF receptors R1, R2 and R3.

EXAMPLE 3

PDGF Beta-receptor Phosphorylation

To test if PDGF-D causes increased phosphorylation of the PDGF beta-receptor, truncated PDGF-D was tested for its capacity to bind to the PDGF beta-receptor and stimulate increased phosphorylation. Serum-starved porcine aortic endothelial-1 (PAE-1) cells stably expressing the human PDGF beta-receptor (Eriksson et al., EMBO J, 1992, 11, 543–550) were incubated on ice for 90 minutes with a solution of conditioned media mixed with an equal volume of PBS supplemented with 1 mg/ml BSA. The conditioned media was prepared from COS cells transfected with expression vectors for PDGF-A or truncated PDGF-D (as constructed in Example 1), or a mock control vector. Twenty-four hours after transfection, the medium was replaced by serum-free medium containing 1 mg/ml serum albumin. Conditioned medium was harvested after an additional 48 hours of incubation. Sixty minutes after the addition of the conditioned media, the cells were lysed in lysis buffer (20 mM tris-HCl, pH 7.5, 0.5% Triton X-100, 0.5% deoxycholic acid, 10 mM EDTA, 1 mM orthovanadate, 1 mM PMSF 1% Trasylol). The PDGF beta-receptors were immunoprecipitated from cleared lysates with rabbit antisera against the human PDGF beta-receptor (Eriksson et al., EMBO J, 1992 11 543–550). The precipitated receptors were applied to a SDS-PAGE gel. After SDS gel electrophoresis, the precipitated receptors were transferred to nitrocellulose filters, and the filters were probed with anti-phosphotyrosine antibody PY-20, (Transduction Laboratories). The filters were then incubated with horseradish peroxidase-conjugated anti-mouse antibodies. Bound antibodies were detected using enhanced chemiluminescence (ECL, Amersham Inc). The filters were then stripped and reprobed with the PDGF beta-receptor rabbit antisera, and the amount of receptors was determined by incubation with horseradish peroxidase-conjugated anti-rabbit antibodies. Bound antibodies were detected using enhanced chemiluminescence (ECL, Amersham Inc). The probing of the filters with PDGF beta receptor antibodies confirmed that equal amounts of the receptor were present in all lanes. Human recombinant PDGF-BB (100 ng/ml) and untreated cells were included in the experiment as a control. FIG. 11 shows that truncated PDGF-D containing conditioned medium stimulated PDGF beta-receptor tyrosine phosphorylation. This indicates that truncated PDGF-D is a PDGF beta-receptor ligand/agonist.

EXAMPLE 4

Competitive Binding Assay

Figure 12:
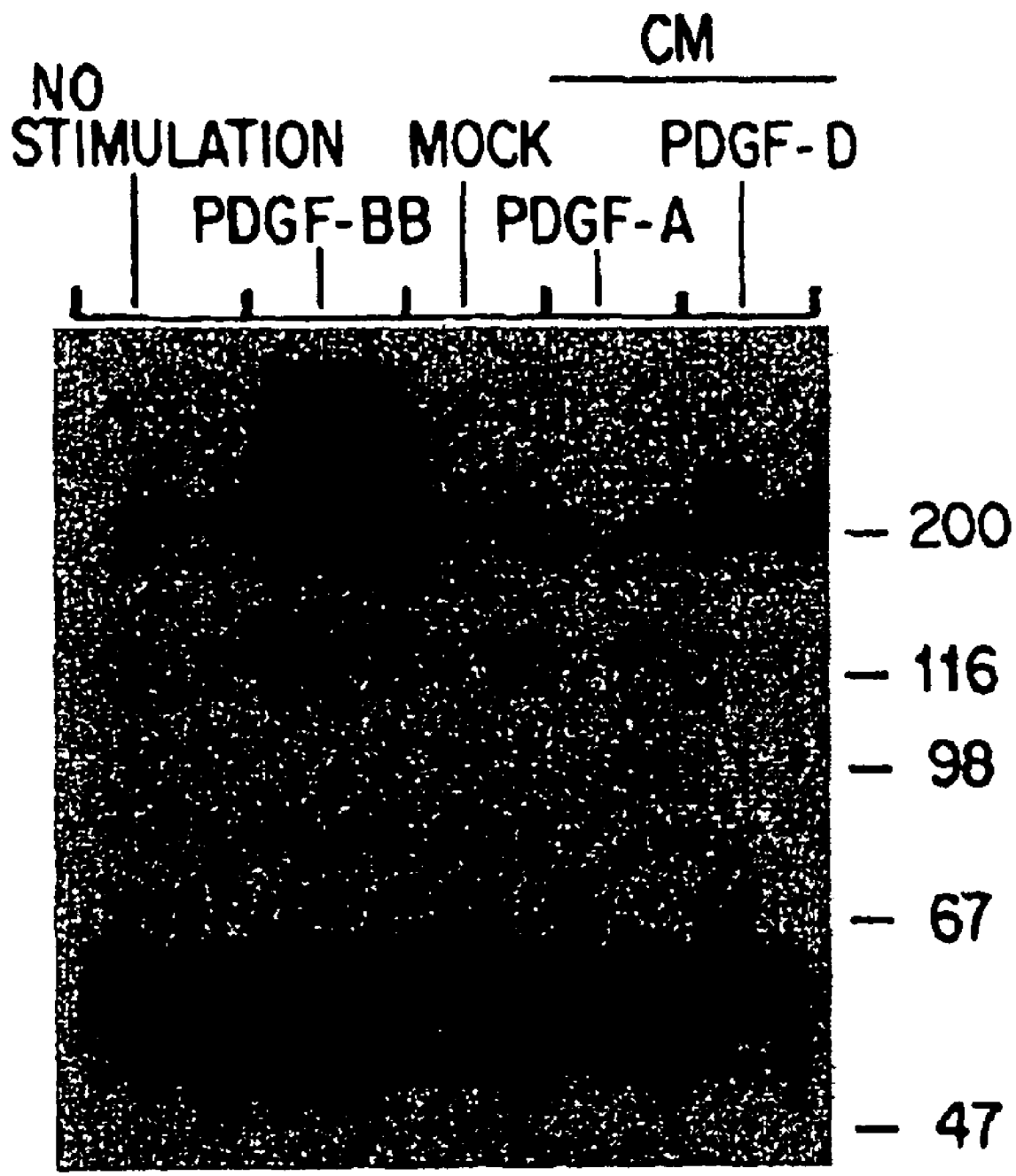
FIG. 12 shows that conditioned medium (CM) containing truncated PDGF-D stimulates tyrosine phosphorylation of PDGF beta-receptors in PAE-1 cells.
Figure 13:
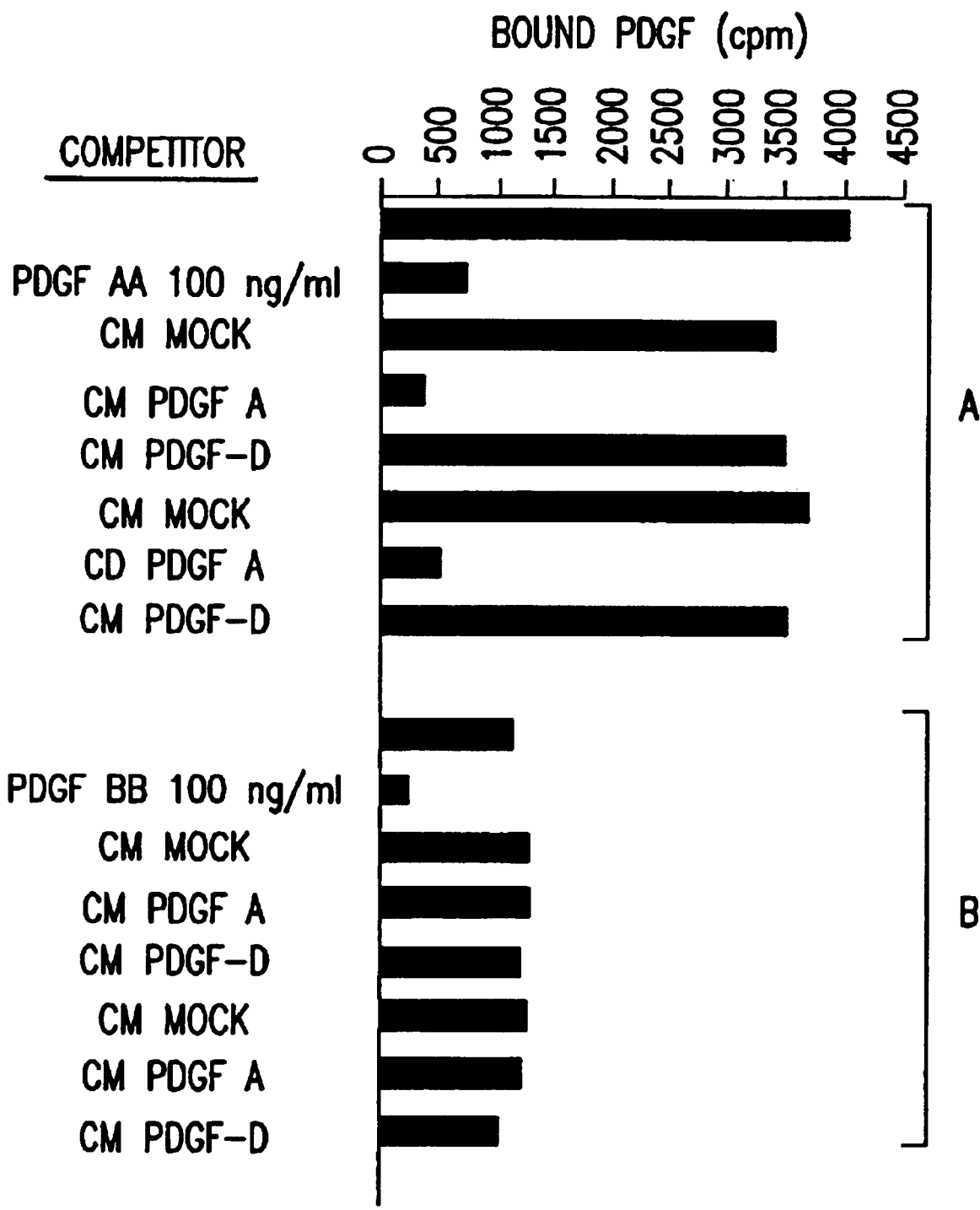
FIG. 13 provides a graphical representation of results which show that conditioned medium (CM) containing truncated PDGF-D competes for binding with PDGF-BB homodimers for the PDGF beta-receptors, but not with PDGF-AA homodimers for the PDGF alpha-receptors.

Next, truncated PDGF-D was tested for its capacity to bind to the human PDGF beta-receptor by analyzing its ability to compete with PDGF-BB for binding to the PDGF beta-receptor. The binding experiments were performed on porcine aortic endothelial-1 (PAE-1) cells stably expressing the human PDGF alpha- and beta-receptors, respectively (Eriksson et al., EMBO J, 1992, 11, 543–550). Binding experiments were performed essentially as in Heldin et al. (EMBO J, 1988, 7 1387–1393). Conditioned media from COS cells expressing PDGF-A, truncated PDGF-D, or mock control, respectively, was diluted with an equal volume of BSA/PBS and mixed with 100 ng/ml of $^{125}$I-PDGF-BB (beta-receptor ligand) or of $^{125}$I-PDGF-AA (alpha-receptor ligand) in binding buffer (PBS containing 1 mg/ml of BSA) Two separate sets of conditioned media from these COS cells were analyzed. Aliquots were incubated with the receptor expressing PAE-1 cells plated in 24-well culture dishes on ice for 90 minutes. After three washes with binding buffer, cell-bound $^{125}$I-PDGF-BB or $^{125}$I-PDGF-AA was extracted by lysis of cells in 20 mM Tris-HCl, pH 7.5, 10% glycerol, 1% Triton X-100. The amount of cell bound radioactivity was determined in a gamma-counter. FIG. 12 provides a graphical representation of results which show that conditioned medium containing truncated PDGF-D competes for binding with PDGF-BB homodimers for the PDGF beta-receptors, but not with PDGF-AA homodimers for the PDGF alpha-receptors.

PDGF-D does not bind to any of the known VEGF receptors. PDGF-D is the only VEGF family member, thus far, which can bind to and increase phosphorylation of the PDGF beta-receptor. These characteristics indicate that the truncated form of PDGF-D may not be a VEGF family member, but instead a novel PDGF. Furthermore, the full length protein is likely to be a latent growth factor that needs to be activated by proteolytic processing to release the active PDGF/VEGF homology domain. The N-terminal CUB domain may be expressed as an inhibitory domain which might be used to localize this latent growth factor in some extracellular compartment (for example the extracellular matrix) and which is removed by limited proteolysis when need, for example during embryonic development, tissue regeneration, tissue remodelling including bone remodelling, active angiogenesis, tumor progression, tumor invasion, metastasis formation and/or wound healing.

BIOASSAYS TO DETERMINE THE FUNCTION OF PDGF-D

Assays are conducted to evaluate whether PDGF-D has similar activities to PDGF-A, PDGF-B, VEGF, VEGF-B, VEGF-C and/or VEGF-D in relation to growth and/or motility of connective tissue cells, fibroblasts, myofibroblasts and glial cells; to endothelial cell function; to angiogenesis; and to wound healing. Further assays may also be performed, depending on the results of receptor binding distribution studies.

I. Mitogenicity of PDGF-D for Endothelial Cells

To test the mitogenic capacity of PDGF-D for endothelial cells, the PDGF-D polypeptide is introduced into cell culture medium containing 5% serum and applied to bovine aortic endothelial cells (BAEs) propagated in medium containing 10% serum. The BAEs are previously seeded in 24-well dishes at a density of 10,000 cells per well the day before addition of the PDGF-D. Three days after addition of this polypeptide the cells were dissociated with trypsin and counted. Purified VEGF is included in the experiment as positive control.

II. Mitogenicity of PDGF-D for Fibroblasts

To test the mitogenic capacity of PDGF-D for fibroblasts, different concentrations of truncated homodimers of PDGF-DD or PDGF-AA (as control) are added to serum starved human foreskin fibroblasts in the presence of 0.2 μmCi [3H]thymidine. The fibroblasts are then incubated for 24 hours with 1 ml of serum-free medium supplemented with 1 mg/ml BSA. After trichloroacetic acid (TCA) precipitation, the incorporation of [3H]thymidine into DNA is determined using a beta-counter. The assay is performed essentially as described in Mori et al., J. Biol. Chem., 1991 266 21158–21164.

III. Assays of Endothelial Cell Function a) Endothelial Cell Proliferation

Endothelial cell growth assays are performed by methods well known in the art, e.g. those of Ferrara & Henzel, Nature, 1989 380 439–443, Gospodarowicz et al., Proc. Natl. Acad. Sci. USA, 1989 86 7311–7315, and/or Claffey et al., Biochem. Biophys. Acta, 1995 1246 1–9.

b) Cell Adhesion Assay

The effect of PDGF-D on adhesion of polymorphonuclear granulocytes to endothelial cells is tested.

c) Chemotaxis

The standard Boyden chamber chemotaxis assay is used to test the effect of PDGF-D on chemotaxis.

d) Plasminogen Activator Assay

Endothelial cells are tested for the effect of PDGF-D on plasminogen activator and plasminogen activator inhibitor production, using the method of Pepper et al., Biochem. Biophys. Res. Commun., 1991 181 902–906.

e) Endothelial Cell Migration Assay

The ability of PDGF-D to stimulate endothelial cells to migrate and form tubes is assayed as described in Montesano et al., Proc. Natl. Acad. Sci. USA, 1986 83 7297–7301. Alternatively, the three-dimensional collagen gel assay described in Joukov et al., EMBO J., 1996 15 290–298 or a gelatinized membrane in a modified Boyden chamber (Glaser et al., Nature, 1980 288 483–484) may be used.

IV. Angiogenesis Assay

The ability of PDGF-D to induce an angiogenic response in chick chorioallantoic membrane is tested as described in Leung et al., Science, 1989 246 1306–1309. Alternatively the rat cornea assay of Rastinejad et al., Cell, 1989 56 345–355 may be used; this is an accepted method for assay of in vivo angiogenesis, and the results are readily transferrable to other in vivo systems.

V. Wound Healing

The ability of PDGF-D to stimulate wound healing is tested in the most clinically relevant model available, as described in Schilling et al., Surgery, 1959 46 702–710 and utilized by Hunt et al., Surgery, 1967 114 302–307.

VI. The Haemopoietic System

A variety of in vitro and in vivo assays using specific cell populations of the haemopoietic system are known in the art, and are outlined below. In particular a variety of in vitro murine stem cell assays using fluorescence-activated cell sorter to purified cells are particularly convenient:

a) Repopulating Stem Cells

These are cells capable of repopulating the bone marrow of lethally irradiated mice, and have the Lin$^-$, Rh$^{h1}$, Ly-6A/E$^+$, c-kit$^+$ phenotype. PDGF-D is tested on these cells either alone, or by co-incubation with other factors, followed by measurement of cellular proliferation by $^3$H-thymidine incorporation.

b) Late Stage Stem Cells

These are cells that have comparatively little bone marrow repopulating ability, but can generate D13 CFU-S. These cells have the Lin$^-$, Rh$^{h1}$, Ly-6A/E$^+$, c-kit$^+$ phenotype. PDGF-D is incubated with these cells for a period of time, injected into lethally irradiated recipients, and the number of D13 spleen colonies enumerated.

c) Progenitor-Enriched Cells

These are cells that respond in vitro to single growth factors and have the Lin$^-$, Rh$^{h1}$, Ly-6A/E$^+$, c-kit$^+$ phenotype. This assay will show if PDGF-D can act directly on haemopoietic progenitor cells. PDGF-D is incubated with these cells in agar cultures, and the number of colonies present after 7–14 days is counted.

VII. Atherosclerosis

Smooth muscle cells play a crucial role in the development or initiation of atherosclerosis, requiring a change of their phenotype from a contractile to a synthetic state. Macrophages, endothelial cells, T lymphocytes and platelets all play a role in the development of atherosclerotic plaques by influencing the growth and phenotypic modulations of smooth muscle cell. An in vitro assay using a modified Rose chamber in which different cell types are seeded on to opposite cover slips measures the proliferative rate and phenotypic modulations of smooth muscle cells in a multicellular environment, and is used to assess the effect of PDGF-D on smooth muscle cells.

VIII. Metastasis

The ability of PDGF-D to inhibit metastasis is assayed using the Lewis lung carcinoma model, for example using the method of Cao et al., J. Exp. Med., 1995 182 2069–2077.

IX. Migration of Smooth Muscle Cells

The effects of the PDGF-D on the migration of smooth muscle cells and other cells types can be assayed using the method of Koyama et al., J. Biol. Chem., 1992 267 22806–22812.

X. Chemotaxis

The effects of the PDGF-D on chemotaxis of fibroblast, monocytes, granulocytes and other cells can be assayed using the method of Siegbahn et al., J. Clin. Invest., 1990 85 916–920.

XI. PDGF-D in Other Cell Types

The effects of PDGF-D on proliferation, differentiation and function of other cell types, such as liver cells, cardiac muscle and other cells, endocrine cells and osteoblasts can readily be assayed by methods known in the art, such as $^3$H-thymidine uptake by in vitro cultures.

XII. Construction of PDGF-D Variants and Analogues

PDGF-D is a member of the PDGF family of growth factors which exhibits a high degree of homology to the other members of the PDGF family. PDGF-D contains seven conserved cysteine residues which are characteristic of this family of growth factors. These conserved cysteine residues form intra-chain disulfide bonds which produce the cysteine knot structure, and inter-chain disulfide bonds that form the protein dimers which are characteristic of members of the PDGF family of growth factors. PDGF-D interacts with a protein tyrosine kinase growth factor receptor.

In contrast to proteins where little or nothing is known about the protein structure and active sites needed for receptor binding and consequent activity, the design of active mutants of PDGF-D is greatly facilitated by the fact that a great deal is known about the active sites and important amino acids of the members of the PDGF family of growth factors.

Published articles elucidating the structure/activity relationships of members of the PDGF family of growth factors include for PDGF: Oestman et al., J. Biol. Chem., 1991 266 10073–10077; Andersson et al., J. Biol. Chem., 1992 267 11260–1266; Oefner et al., EMBO J., 1992 11 3921–3926; Flemming et al., Molecular and Cell Biol., 1993 13 4066–4076 and Andersson et al., Growth Factors, 1995 12 159–164; and for VEGF: Kim et al., Growth Factors, 1992 7 53–64; Pötgens et al., J. Biol. Chem., 1994 269 32879–32885 and Claffey et al., Biochem. Biophys. Acta, 1995 1246 1–9. From these publications it is apparent that because of the eight conserved cysteine residues, the members of the PDGF family of growth factors exhibit a characteristic knotted folding structure and dimerization, which result in formation of three exposed loop regions at each end of the dimerized molecule, at which the active receptor binding sites can be expected to be located.

Based on this information, a person skilled in the biotechnology arts can design PDGF-D mutants with a very high probability of retaining PDGF-D activity by conserving the eight cysteine residues responsible for the knotted folding arrangement and for dimerization, and also by conserving, or making only conservative amino acid substitutions in the likely receptor sequences in the loop 1, loop 2 and loop 3 region of the protein structure.

The formation of desired mutations at specifically targeted sites in a protein structure is considered to be a standard technique in the arsenal of the protein chemist (Kunkel et al., Methods in Enzymol., 1987 154 367–382). Examples of such site-directed mutagenesis with VEGF can be found in Pötgens et al., J. Biol. Chem., 1994 269 32879–32885 and Claffey et al., Biochem. Biophys. Acta, 1995 1246 1–9. Indeed, site-directed mutagenesis is so common that kits are commercially available to facilitate such procedures (e.g. Promega 1994–1995 Catalog., Pages 142–145).

The connective tissue cell, fibroblast, myofibroblast and glial cell growth and/or motility activity, the endothelial cell proliferation activity, the angiogenesis activity and/or the wound healing activity of PDGF-D mutants can be readily confirmed by well established screening procedures. For example, a procedure analogous to the endothelial cell mitotic assay described by Claffey et al., (Biochem. Biophys. Acta., 1995 1246 1–9) can be used. Similarly the effects of PDGF-D on proliferation of other cell types, on cellular differentiation and on human metastasis can be tested using methods which are well known in the art.

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations falling within the scope of the appended claims and equivalents thereof.

What is claimed is:

1. An isolated polypeptide comprising the amino acid sequence of SEQ ID NO: 4, the amino acid sequence of SEQ ID NO: 6, or the amino acid sequence of SEQ ID NO: 8.

2. An isolated polypeptide according to claim 1, wherein said polypeptide is a human polypeptide.

3. An isolated polypeptide according to claim 1, wherein said polypeptide stimulates or enhances at least one function selected from the group consisting of proliferation, differentiation, growth, and motility of cells expressing a platelet-derived growth factor D (PDGF-D) receptor.

4. An isolated polypeptide according to claim 3, wherein the cells are selected from the group consisting of endothelial cells, connective tissue cells, myofibroblasts and glial cells.

5. An isolated polypeptide according to claim 1, which comprises the characteristic sequence

PXCLLVXRCGGNCXC (SEQ ID NO: 25).

6. An isolated polypeptide according to claim 1, wherein said polypeptide comprises a fragment or analog of SEQ ID NO: 8 having the ability to stimulate one or more of proliferation, differentiation, motility, or survival of cells expressing a PDGF-D receptor, said fragment or analog comprising amino acids 234–370 of SEQ ID NO: 8.

7. An isolated polypeptide according to claim 1, wherein said polypeptide comprises a fragment or analog of SEQ ID NO: 8 having the ability to stimulate one or more of proliferation, differentiation, motility, or survival of cells expressing a PDGF-D receptor, said fragment or analog comprising amino acids 255–370 of SEQ ID NO: 8.

8. An isolated polypeptide produced by expression of a polynucleotide comprising at least nucleotides 1 to 600 of the sequence of SEQ ID NO: 3, at least nucleotides 1–966 of the sequence of SEQ ID NO: 5, at least nucleotides 176–1285 of SEQ ID NO: 7 or at least nucleotides 935 to 1285 of SEQ ID NO: 7.

9. An isolated polypeptide dimer comprising a polypeptide according to claim 1 or claim 8.

10. An isolated polypeptide dimer according to claim 9, wherein said polypeptide dimer is a homodimer of said polypeptide.

11. An isolated polypeptide dimer according to claim 9, wherein said polypeptide dimer is a heterodimer of said polypeptide and vascular endothelial growth factor (VEGF), VEGF-B, VEGF-C, VEGF-D, PDGF-A, PDGF-B or placenta growth factor (PlGF).

12. An isolated polypeptide dimer according to claim 9, wherein said polypeptide dimer is a disulfide-linked dimer.

13. A pharmaceutical composition comprising an effective cell proliferation promoting amount of a polypeptide according to claim 1, claim 8 or claim 5, and at least one further growth factor selected from the group consisting of VEGF, VEGF-B, VEGF-C, VEGF-D, PDGF-A, PDGF-B or PlGF.

14. A pharmaceutical composition according to claim 13, further comprising heparin.

15. A pharmaceutical composition comprising an effective cell proliferation promoting amount of an isolated polypeptide according to claim 1, claim 8 or claim 5, and at least one pharmaceutical carrier or diluent.

16. A pharmaceutical composition according to claim 15, further comprising heparin.

17. A pharmaceutical composition comprising an effective amount of an isolated polypeptide according to claim 1, claim 8 or claim 5 and heparin.

18. A pharmaceutical composition comprising a PDGF receptor stimulating amount of an isolated polypeptide according to claim 1, claim 8 or claim 5, and at least one pharmaceutical carrier or diluent.

19. An isolated polypeptide according to any one of claim 1, claim 8 or claim 5 which comprises a proteolytic site having the amino acid sequence RKSK (SEQ ID NO: 9).

20. An isolated polypeptide which comprises SEQ ID NO: 25 and is encoded by a polynucleotide which remains hybridized at a washing condition of 42° C. in 0.2×SSC with a polynucleotide sequence selected from the group consisting of at least nucleotides 1 to 600 of the sequence set out in FIG. 3 (SEQ ID NO: 3), at least nucleotides at least nucleotides 556–966 set out in FIG. 5 (SEQ ID NO: 5), and at least nucleotides 938 to 1288 set out in FIG. 7 (SEQ ID NO: 7), said polypeptide having the ability to stimulate one or more of proliferation, differentiation, motility, or survival of cells expressing a PDGF-D receptor.

21. An isolated polypeptide having the ability to stimulate one or more of proliferation, differentiation, motility, or survival of cells expressing a PDGF-D receptor, said polypeptide comprising SEQ ID NO: 25 and having at least 85% identity with the amino acid sequence of SEQ ID NO: 4, the amino acid sequence of SEQ ID NO: 6, or the amino acid sequence of SEQ ID NO: 8.

22. An isolated polypeptide having the ability to stimulate one or more of proliferation, differentiation, motility, or survival of cells expressing a PDGF-D receptor, comprising SEQ ID NO: 25 and encoded by a polynucleotide comprising the polynucleotide sequence having at least 85% identity with at least nucleotides 1 to 600 of the sequence set out SEQ ID NO: 3, at least nucleotides 176–1285 of SEQ ID NO: 5 or at least nucleotides 985 to 1285 set out in SEQ ID NO: 7.

* * * * *

```
                              SEQUENCE LISTING

<160> NUMBER OF SEQ ID NOS: 31

<210> SEQ ID NO 1
<211> LENGTH: 360
<212> TYPE: DNA
<213> ORGANISM: Homo sapiens

<400> SEQUENCE: 1
aattgtggct gtggaactgt caactggagg tcctgcacat gcaattcagg gaaaaccgtg     60
aaaaagtatc atgaggtatt acagtttgag cctggccaca tcaagaggag gggtagagct    120
aagaccatgg ctctagttga catccagttg gatcaccatg aacgatgtga ttgtatctgc    180
agctcaagac cacctcgata agagaatgtg cacatcctta cattaagcct gaaagaacca    240
ttagtttaag gagggtgaga taagagaccc ttttcctacc agcaaccaga cttactacta    300
gcctgcaatg caatgaacac aagtggttgc tgagtctcag ccttgctttg ttaatgccat    360

<210> SEQ ID NO 2
<211> LENGTH: 66
<212> TYPE: PRT
<213> ORGANISM: Homo sapiens

<400> SEQUENCE: 2

Asn Cys Gly Cys Gly Thr Val Asn Trp Arg Ser Cys Thr Cys Asn Ser
  1               5                  10                  15

Gly Lys Thr Val Lys Lys Tyr His Glu Val Leu Gln Phe Glu Pro Gly
             20                  25                  30

His Ile Lys Arg Arg Gly Arg Ala Lys Thr Met Ala Leu Val Asp Ile
        35                  40                  45
```

```
Gln Leu Asp His His Glu Arg Cys Asp Cys Ile Cys Ser Ser Arg Pro
        50                  55                  60

Pro Arg
 65

<210> SEQ ID NO 3
<211> LENGTH: 690
<212> TYPE: DNA
<213> ORGANISM: Homo sapiens

<400> SEQUENCE: 3
ggaagatttc caacccgcag cagcttcaga gaccaactgg aatctgtcac aagctctgtt      60
tcagggtatc cctataactc tccatcagta acggatccca ctctgattgc ggatgctctg     120
gacaaaaaaa ttgcagaatt tgatacagtg gaagatctgc tcaagtactt caatccagag     180
tcatggcaag aagatcttga gaatatgtat ctggacaccc ctcggtatcg aggcaggtca     240
taccatgacc ggaagtcaaa agttgacctg gataggctca atgatgatgc aagcgttac      300 agttgcactc ccaggaatta ctcggtcaat ataagaaag agctgaagtt ggccaatgtg      360
gtcttctttc cacgttgcct cctcgtgcag cgctgtggag gaaattgtgg ctgtggaact     420
gtcaaactgg agtcctgcac atgcaattca gggaaaaccg tgaaaaagta tcatgagta      480 ttacagtttg agcctggcca catcaagagg aggggtagag ctaagaccat ggctctagtt     540
gacatccagt tggatcacca tgaacgatgc gattgtatct gcagctcaag accacctcga     600
taagagaatg tgcacatcct tacattaagc ctgaaagaac ctttagttta aggagggtga     660
gataagagac ccttttccta ccagcaaccc                                      690

<210> SEQ ID NO 4
<211> LENGTH: 200
<212> TYPE: PRT
<213> ORGANISM: Homo sapiens

<400> SEQUENCE: 4

Gly Arg Phe Pro Thr Arg Ser Ser Phe Arg Asp Gln Leu Glu Ser Val
 1               5                  10                  15

Thr Ser Ser Val Ser Gly Tyr Pro Tyr Asn Ser Pro Val Thr Asp
            20                  25                  30

Pro Thr Leu Ile Ala Asp Ala Leu Asp Lys Lys Ile Ala Glu Phe Asp
        35                  40                  45

Thr Val Glu Asp Leu Leu Lys Tyr Phe Asn Pro Glu Ser Trp Gln Glu
    50                  55                  60

Asp Leu Glu Asn Met Tyr Leu Asp Thr Pro Arg Tyr Arg Gly Arg Ser
 65                  70                  75                  80

Tyr His Asp Arg Lys Ser Lys Val Asp Leu Asp Arg Leu Asn Asp Asp
                 85                  90                  95

Ala Lys Arg Tyr Ser Cys Thr Pro Arg Asn Tyr Ser Val Asn Ile Arg
            100                 105                 110

Glu Glu Leu Lys Leu Ala Asn Val Phe Phe Pro Arg Cys Leu Leu
        115                 120                 125

Val Gln Arg Cys Gly Gly Asn Cys Gly Cys Thr Val Lys Leu Glu
    130                 135                 140

Ser Cys Thr Cys Asn Ser Gly Lys Thr Val Lys Lys Tyr His Glu Val
145                 150                 155                 160

Leu Gln Phe Glu Pro Gly His Ile Lys Arg Arg Gly Arg Ala Lys Thr
                165                 170                 175
```

```
Met Ala Leu Val Asp Ile Gln Leu Asp His His Glu Arg Cys Asp Cys
            180                 185                 190
Ile Cys Ser Ser Arg Pro Pro Arg
        195                 200

<210> SEQ ID NO 5
<211> LENGTH: 1934
<212> TYPE: DNA
<213> ORGANISM: Homo sapiens
<220> FEATURE:
<221> NAME/KEY: CDS
<222> LOCATION: (1)..(966)

<400> SEQUENCE: 5 ttg tac cga aga gat gag acc atc cag gtg aaa gga aac ggc tac gtg        48
Leu Tyr Arg Arg Asp Glu Thr Ile Gln Val Lys Gly Asn Gly Tyr Val
  1               5                  10                  15 cag agt cct aga ttc ccg aac agc tac ccc agg aac ctg ctc ctg aca        96
Gln Ser Pro Arg Phe Pro Asn Ser Tyr Pro Arg Asn Leu Leu Leu Thr
             20                  25                  30 tgg cgg ctt cac tct cag gag aat aca cgg ata cag cta gtg ttt gac       144
Trp Arg Leu His Ser Gln Glu Asn Thr Arg Ile Gln Leu Val Phe Asp
         35                  40                  45 aat cag ttt gga tta gag gaa gca gaa aat gat atc tgt agg tat gat       192
Asn Gln Phe Gly Leu Glu Glu Ala Glu Asn Asp Ile Cys Arg Tyr Asp
     50                  55                  60 ttt gtg gaa gtt gaa gat ata tcc gaa acc agt acc att att aga gga       240
Phe Val Glu Val Glu Asp Ile Ser Glu Thr Ser Thr Ile Ile Arg Gly
 65                  70                  75                  80 cga tgg tgt gga cac aag gaa gtt cct cca agg ata aaa tca aga acg       288
Arg Trp Cys Gly His Lys Glu Val Pro Pro Arg Ile Lys Ser Arg Thr
                 85                  90                  95 aac caa att aaa atc aca ttc aag tcc gat gac tac ttt gtg gct aaa       336
Asn Gln Ile Lys Ile Thr Phe Lys Ser Asp Asp Tyr Phe Val Ala Lys
            100                 105                 110 cct gga ttc aag att tat tat tct ttg ctg gaa gat ttc caa ccc gca       384
Pro Gly Phe Lys Ile Tyr Tyr Ser Leu Leu Glu Asp Phe Gln Pro Ala
        115                 120                 125 gca gct tca gag acc aac tgg gaa tct gtc aca agc tct att tca ggg       432
Ala Ala Ser Glu Thr Asn Trp Glu Ser Val Thr Ser Ser Ile Ser Gly
    130                 135                 140 gta tcc tat aac tct cca tca gta acg gat ccc act ctg att gcg gat       480
Val Ser Tyr Asn Ser Pro Ser Val Thr Asp Pro Thr Leu Ile Ala Asp
145                 150                 155                 160 gct ctg gac aaa aaa att gca gaa ttt gat aca gtg gaa gat ctg ctc       528
Ala Leu Asp Lys Lys Ile Ala Glu Phe Asp Thr Val Glu Asp Leu Leu
                165                 170                 175 aag tac ttc aat cca gag tca tgg caa gaa gat ctt gag aat atg tat       576
Lys Tyr Phe Asn Pro Glu Ser Trp Gln Glu Asp Leu Glu Asn Met Tyr
            180                 185                 190 ctg gac acc cct cgg tat cga ggc agg tca tac cat gac cgg aag tca       624
Leu Asp Thr Pro Arg Tyr Arg Gly Arg Ser Tyr His Asp Arg Lys Ser
        195                 200                 205 aaa gtt gac ctg gat agg ctc aat gat gat gcc aag cgt tac agt tgc       672
Lys Val Asp Leu Asp Arg Leu Asn Asp Asp Ala Lys Arg Tyr Ser Cys
    210                 215                 220 act ccc agg aat tac tcg gtc aat ata aga gaa gag ctg aag ttg gcc       720
Thr Pro Arg Asn Tyr Ser Val Asn Ile Arg Glu Glu Leu Lys Leu Ala
225                 230                 235                 240 aat gtg gtc ttc ttt cca cgt tgc ctc ctc gtg cag cgc tgt gga gga       768
```

```
              Asn Val Val Phe Phe Pro Arg Cys Leu Leu Val Gln Arg Cys Gly Gly
                              245                 250                 255
aat tgt ggc tgt gga act gtc aac tgg agg tcc tgc aca tgc aat tca       816
Asn Cys Gly Cys Gly Thr Val Asn Trp Arg Ser Cys Thr Cys Asn Ser
                260                 265                 270 ggg aaa acc gtg aaa aag tat cat gag gta tta cag ttt gag cct ggc       864
Gly Lys Thr Val Lys Lys Tyr His Glu Val Leu Gln Phe Glu Pro Gly
            275                 280                 285 cac atc aag agg agg ggt aga gct aag acc atg gct cta gtt gac atc       912
His Ile Lys Arg Arg Gly Arg Ala Lys Thr Met Ala Leu Val Asp Ile
        290                 295                 300 cag ttg gat cac cat gaa cga tgc gat tgt atc tgc agc tca aga cca       960
Gln Leu Asp His His Glu Arg Cys Asp Cys Ile Cys Ser Ser Arg Pro
305                 310                 315                 320 cct cga taagagaatg tgcacatcct tacattaagc ctgaaagaac ctttagttta       1016
Pro Arg aggagggtga gataagagac ccttttccta ccagcaacca aacttactac tagcctgcaa    1076
tgcaatgaac acaagtggtt gctgagtctc agccttgctt tgttaatgcc atggcaagta    1136
gaaaggtata tcatcaactt ctatacctaa gaatatagga ttgcatttaa taatagtgtt    1196
tgaggttata tatgcacaaa cacacacaga aatatattca tgtctatgtg tatatagatc    1256
aaatgttttt tttggtatat ataaccaggt acaccgagc ttacatatgt ttgagttaga     1316
ctcttaaaat cctttgccaa ataagggat ggtcaaatat atgaaacatg tctttagaaa     1376
atttaggaga taaattatt tttaaatttt gaaacacaaa acaattttga atcttgctct     1436
cttaaagaaa gcatcttgta tattaaaaat caaaagatga ggctttctta catatacatc    1496
ttagttgatt attaaaaaag gaaaaaggtt tccagagaaa aggccaatac ctaagcattt    1556
tttccatgag aagcactgca tacttaccta tgtggactgt ataacctgt ctccaaaacc     1616 atgccataat aatataagtg ctttagaaat taaatcattg tgttttttat gcattttgct    1676
gaggcatcct tattcattta acacctatct caaaaactta cttagaaggt tttttattat    1736
agtcctacaa aagacaatgt ataagctgta acagaatttt gaattgtttt tctttgcaaa    1796
acccctccac aaaagcaaat cctttcaaga atggcatggg cattctgtat gaacctttcc    1856
agatggtgtt cagtgaaaga tgtgggtagt tgagaactta aaaagtgaac attgaaacat    1916
cgacgtaact ggaaaccg                                                  1934

<210> SEQ ID NO 6
<211> LENGTH: 322
<212> TYPE: PRT
<213> ORGANISM: Homo sapiens

<400> SEQUENCE: 6

Leu Tyr Arg Arg Asp Glu Thr Ile Gln Val Lys Gly Asn Gly Tyr Val
 1               5                  10                  15

Gln Ser Pro Arg Phe Pro Asn Ser Tyr Pro Arg Asn Leu Leu Leu Thr
                20                  25                  30

Trp Arg Leu His Ser Gln Glu Asn Thr Arg Ile Gln Leu Val Phe Asp
            35                  40                  45

Asn Gln Phe Gly Leu Glu Glu Ala Glu Asn Asp Ile Cys Arg Tyr Asp
        50                  55                  60

Phe Val Glu Val Glu Asp Ile Ser Glu Thr Ser Thr Ile Ile Arg Gly
65                  70                  75                  80

Arg Trp Cys Gly His Lys Glu Val Pro Pro Arg Ile Lys Ser Arg Thr
                85                  90                  95
```

```
Asn Gln Ile Lys Ile Thr Phe Lys Ser Asp Asp Tyr Phe Val Ala Lys
            100                 105                 110
Pro Gly Phe Lys Ile Tyr Tyr Ser Leu Leu Glu Asp Phe Gln Pro Ala
        115                 120                 125
Ala Ala Ser Glu Thr Asn Trp Glu Ser Val Thr Ser Ile Ser Gly
    130                 135                 140
Val Ser Tyr Asn Ser Pro Ser Val Thr Asp Pro Thr Leu Ile Ala Asp
145                 150                 155                 160
Ala Leu Asp Lys Lys Ile Ala Glu Phe Asp Thr Val Glu Asp Leu Leu
                165                 170                 175
Lys Tyr Phe Asn Pro Glu Ser Trp Gln Glu Asp Leu Glu Asn Met Tyr
            180                 185                 190
Leu Asp Thr Pro Arg Tyr Arg Gly Arg Ser Tyr His Asp Arg Lys Ser
        195                 200                 205
Lys Val Asp Leu Asp Arg Leu Asn Asp Ala Lys Arg Tyr Ser Cys
210                 215                 220
Thr Pro Arg Asn Tyr Ser Val Asn Ile Arg Glu Leu Lys Leu Ala
225                 230                 235                 240
Asn Val Val Phe Phe Pro Arg Cys Leu Leu Val Gln Arg Cys Gly Gly
                245                 250                 255
Asn Cys Gly Cys Gly Thr Val Asn Trp Arg Ser Cys Thr Cys Asn Ser
            260                 265                 270
Gly Lys Thr Val Lys Lys Tyr His Glu Val Leu Gln Phe Glu Pro Gly
        275                 280                 285
His Ile Lys Arg Arg Gly Arg Ala Lys Thr Met Ala Leu Val Asp Ile
    290                 295                 300
Gln Leu Asp His His Glu Arg Cys Asp Cys Ile Cys Ser Ser Arg Pro
305                 310                 315                 320
Pro Arg

<210> SEQ ID NO 7
<211> LENGTH: 2253
<212> TYPE: DNA
<213> ORGANISM: Homo sapiens
<220> FEATURE:
<221> NAME/KEY: CDS
<222> LOCATION: (176)..(1288)

<400> SEQUENCE: 7
cgctcggaaa gttcagcatg caggaagttt ggggagagct cggcgattag cacagcgacc      60
cgggccagcg cagggcgagc gcaggcggcg agagcgcagg gcggcgcggc gtcggtcccg     120
ggagcagaac ccggcttttt cttggagcga cgctgtctct agtcgctgat cccaa atg     178
                                                                Met
                                                                  1 cac cgg ctc atc ttt gtc tac act cta atc tgc gca aac ttt tgc agc     226
His Arg Leu Ile Phe Val Tyr Thr Leu Ile Cys Ala Asn Phe Cys Ser
          5                  10                  15 tgt cgg gac act tct gca acc ccg cag agc gca tcc atc aaa gct ttg     274
Cys Arg Asp Thr Ser Ala Thr Pro Gln Ser Ala Ser Ile Lys Ala Leu
         20                  25                  30 cgc aac gcc aac ctc agg cga gat gag agc aat cac ctc aca gac ttg     322
Arg Asn Ala Asn Leu Arg Arg Asp Glu Ser Asn His Leu Thr Asp Leu
     35                  40                  45 tac cga aga gat gag acc atc cag gtg aaa gga aac ggc tac gtg cag     370
Tyr Arg Arg Asp Glu Thr Ile Gln Val Lys Gly Asn Gly Tyr Val Gln
 50                  55                  60                  65
```

```
agt cct aga ttc ccg aac agc tac ccc agg aac ctg ctc ctg aca tgg     418
Ser Pro Arg Phe Pro Asn Ser Tyr Pro Arg Asn Leu Leu Leu Thr Trp
             70                  75                  80 cgg ctt cac tct cag gag aat aca cgg ata cag cta gtg ttt gac aat     466
Arg Leu His Ser Gln Glu Asn Thr Arg Ile Gln Leu Val Phe Asp Asn
                 85                  90                  95 cag ttt gga tta gag gaa gca gaa aat gat atc tgt agg tat gat ttt     514
Gln Phe Gly Leu Glu Glu Ala Glu Asn Asp Ile Cys Arg Tyr Asp Phe
                100                 105                 110 gtg gaa gtt gaa gat ata tcc gaa acc agt acc att att aga gga cga     562
Val Glu Val Glu Asp Ile Ser Glu Thr Ser Thr Ile Ile Arg Gly Arg
    115                 120                 125 tgg tgt gga cac aag gaa gtt cct cca agg ata aaa tca aga acg aac     610
Trp Cys Gly His Lys Glu Val Pro Pro Arg Ile Lys Ser Arg Thr Asn
130                 135                 140                 145 caa att aaa atc aca ttc aag tcc gat gac tac ttt gtg gct aaa cct     658
Gln Ile Lys Ile Thr Phe Lys Ser Asp Asp Tyr Phe Val Ala Lys Pro
                150                 155                 160 gga ttc aag att tat tat tct ttg ctg gaa gat ttc caa ccc gca gca     706
Gly Phe Lys Ile Tyr Tyr Ser Leu Leu Glu Asp Phe Gln Pro Ala Ala
            165                 170                 175 gct tca gag acc aac tgg gaa tct gtc aca agc tct att tca ggg gta     754
Ala Ser Glu Thr Asn Trp Glu Ser Val Thr Ser Ser Ile Ser Gly Val
        180                 185                 190 tcc tat aac tct cca tca gta acg gat ccc act ctg att gcg gat gct     802
Ser Tyr Asn Ser Pro Ser Val Thr Asp Pro Thr Leu Ile Ala Asp Ala
    195                 200                 205 ctg gac aaa aaa att gca gaa ttt gat aca gtg gaa gat ctg ctc aag     850
Leu Asp Lys Lys Ile Ala Glu Phe Asp Thr Val Glu Asp Leu Leu Lys
210                 215                 220                 225 tac ttc aat cca gag tca tgg caa gaa gat ctt gag aat atg tat ctg     898
Tyr Phe Asn Pro Glu Ser Trp Gln Glu Asp Leu Glu Asn Met Tyr Leu
                230                 235                 240 gac acc cct cgg tat cga ggc agg tca tac cat gac cgg aag tca aaa     946
Asp Thr Pro Arg Tyr Arg Gly Arg Ser Tyr His Asp Arg Lys Ser Lys
            245                 250                 255 gtt gac ctg gat agg ctc aat gat gat gcc aag cgt tac agt tgc act     994
Val Asp Leu Asp Arg Leu Asn Asp Asp Ala Lys Arg Tyr Ser Cys Thr
        260                 265                 270 ccc agg aat tac tcg gtc aat ata aga gaa gag ctg aag ttg gcc aat    1042
Pro Arg Asn Tyr Ser Val Asn Ile Arg Glu Glu Leu Lys Leu Ala Asn
    275                 280                 285 gtg gtc ttc ttt cca cgt tgc ctc ctc gtg cag cgc tgt gga gga aat    1090
Val Val Phe Phe Pro Arg Cys Leu Leu Val Gln Arg Cys Gly Gly Asn
290                 295                 300                 305 tgt ggc tgt gga act gtc aac tgg agg tcc tgc aca tgc aat tca ggg    1138
Cys Gly Cys Gly Thr Val Asn Trp Arg Ser Cys Thr Cys Asn Ser Gly
                310                 315                 320 aaa acc gtg aaa aag tat cat gag gta tta cag ttt gag cct ggc cac    1186
Lys Thr Val Lys Lys Tyr His Glu Val Leu Gln Phe Glu Pro Gly His
            325                 330                 335 atc aag agg agg ggt aga gct aag acc atg gct cta gtt gac atc cag    1234
Ile Lys Arg Arg Gly Arg Ala Lys Thr Met Ala Leu Val Asp Ile Gln
        340                 345                 350 ttg gat cac cat gaa cga tgc gat tgt atc tgc agc tca aga cca cct    1282
Leu Asp His His Glu Arg Cys Asp Cys Ile Cys Ser Ser Arg Pro Pro
    355                 360                 365 cga taa gagaatgtgc acatccttac attaagcctg aaagaacctt tagtttaagg    1338
Arg
```

```
                                                                         370
agggtgagat aagagaccct tttcctacca gcaaccaaac ttactactag cctgcaatgc         1398
aatgaacaca agtggttgct gagtctcagc cttgctttgt taatgccatg gcaagtagaa         1458
aggtatatca tcaacttcta tacctaagaa tataggattg catttaataa tagtgtttga         1518
ggttatatat gcacaaacac acacagaaat atattcatgt ctatgtgtat atagatcaaa         1578 tgttttttt ggtatatata accaggtaca ccagagctta catatgtttg agttagactc          1638
ttaaaatcct ttgccaaaat aagggatggt caaatatatg aaacatgtct ttagaaaatt         1698
taggagataa atttattttt aaattttgaa acacaaaaca attttgaatc ttgctctctt         1758
aaagaaagca tcttgtatat taaaaatcaa aagatgaggc tttcttacat atacatctta         1818
gttgattatt aaaaaaggaa aaaggtttcc agagaaaagg ccaataccta agcatttttt         1878
ccatgagaag cactgcatac ttacctatgt ggactgtaat aacctgtctc caaaaccatg         1938
ccataataat ataagtgctt tagaaattaa atcattgtgt tttttatgca ttttgctgag         1998
gcatccttat tcatttaaca cctatctcaa aaacttactt agaaggtttt ttattatagt         2058
cctacaaaag acaatgtata agctgtaaca gaattttgaa ttgttttct ttgcaaaacc         2118 cctccacaaa agcaaatcct ttcaagaatg gcatgggcat tctgtatgaa cctttccaga         2178
tggtgttcag tgaaagatgt gggtagttga gaacttaaaa agtgaacatt gaaacatcga         2238
cgtaactgga aaccg                                                          2253
```

`<210> SEQ ID NO 8`
`<211> LENGTH: 370`
`<212> TYPE: PRT`
`<213> ORGANISM: Homo sapiens`

`<400> SEQUENCE: 8`

```
Met His Arg Leu Ile Phe Val Tyr Thr Leu Ile Cys Ala Asn Phe Cys
  1               5                  10                  15

Ser Cys Arg Asp Thr Ser Ala Thr Pro Gln Ser Ala Ser Ile Lys Ala
             20                  25                  30

Leu Arg Asn Ala Asn Leu Arg Arg Asp Glu Ser Asn His Leu Thr Asp
         35                  40                  45

Leu Tyr Arg Arg Asp Glu Thr Ile Gln Val Lys Gly Asn Gly Tyr Val
     50                  55                  60

Gln Ser Pro Arg Phe Pro Asn Ser Tyr Pro Arg Asn Leu Leu Leu Thr
 65                  70                  75                  80

Trp Arg Leu His Ser Gln Glu Asn Thr Arg Ile Gln Leu Val Phe Asp
                 85                  90                  95

Asn Gln Phe Gly Leu Glu Glu Ala Glu Asn Asp Ile Cys Arg Tyr Asp
            100                 105                 110

Phe Val Glu Val Glu Asp Ile Ser Glu Thr Ser Thr Ile Ile Arg Gly
        115                 120                 125

Arg Trp Cys Gly His Lys Glu Val Pro Pro Arg Ile Lys Ser Arg Thr
    130                 135                 140

Asn Gln Ile Lys Ile Thr Phe Lys Ser Asp Asp Tyr Phe Val Ala Lys
145                 150                 155                 160

Pro Gly Phe Lys Ile Tyr Tyr Ser Leu Leu Glu Asp Phe Gln Pro Ala
                165                 170                 175

Ala Ala Ser Glu Thr Asn Trp Glu Ser Val Thr Ser Ser Ile Ser Gly
            180                 185                 190

Val Ser Tyr Asn Ser Pro Ser Val Thr Asp Pro Thr Leu Ile Ala Asp
```

```
                    195                 200                 205
Ala Leu Asp Lys Lys Ile Ala Glu Phe Asp Thr Val Glu Asp Leu Leu
    210                 215                 220

Lys Tyr Phe Asn Pro Glu Ser Trp Gln Glu Asp Leu Glu Asn Met Tyr
225                 230                 235                 240

Leu Asp Thr Pro Arg Tyr Arg Gly Arg Ser Tyr His Asp Arg Lys Ser
                245                 250                 255

Lys Val Asp Leu Asp Arg Leu Asn Asp Asp Ala Lys Arg Tyr Ser Cys
            260                 265                 270

Thr Pro Arg Asn Tyr Ser Val Asn Ile Arg Glu Glu Leu Lys Leu Ala
        275                 280                 285

Asn Val Val Phe Phe Pro Arg Cys Leu Leu Val Gln Arg Cys Gly Gly
    290                 295                 300

Asn Cys Gly Cys Gly Thr Val Asn Trp Arg Ser Cys Thr Cys Asn Ser
305                 310                 315                 320

Gly Lys Thr Val Lys Lys Tyr His Glu Val Leu Gln Phe Glu Pro Gly
                325                 330                 335

His Ile Lys Arg Arg Gly Arg Ala Lys Thr Met Ala Leu Val Asp Ile
            340                 345                 350

Gln Leu Asp His His Glu Arg Cys Asp Cys Ile Cys Ser Ser Arg Pro
        355                 360                 365

Pro Arg
    370

<210> SEQ ID NO 9
<211> LENGTH: 4
<212> TYPE: PRT
<213> ORGANISM: Homo sapiens

<400> SEQUENCE: 9

Arg Lys Ser Lys
  1

<210> SEQ ID NO 10
<211> LENGTH: 192
<212> TYPE: PRT
<213> ORGANISM: Homo sapiens

<400> SEQUENCE: 10

Met Asn Phe Leu Leu Ser Trp Val His Trp Ser Leu Ala Leu Leu Leu
  1               5                  10                  15

Tyr Leu His His Ala Lys Trp Ser Gln Ala Ala Pro Met Ala Glu Gly
                20                  25                  30

Gly Gly Gln Asn His His Glu Val Val Lys Phe Met Asp Val Tyr Gln
            35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Asn Pro Cys Gly
```

```
                    130                 135                 140

Pro Cys Ser Ser Glu Arg Arg Lys His Leu Phe Val Gln Asp Pro Gln
145                 150                 155                 160

Thr Cys Lys Cys Ser Cys Lys Asn Thr Asp Ser Arg Cys Lys Ala Arg
                    165                 170                 175

Gln Leu Glu Leu Asn Glu Arg Thr Cys Arg Cys Asp Lys Pro Arg Arg
                180                 185                 190

<210> SEQ ID NO 11
<211> LENGTH: 170
<212> TYPE: PRT
<213> ORGANISM: Homo sapiens

<400> SEQUENCE: 11

Met Pro Val Met Arg Leu Phe Pro Cys Phe Leu Gln Leu Leu Ala Gly
 1               5                  10                  15

Leu Ala Leu Pro Ala Val Pro Pro Gln Gln Trp Ala Leu Ser Ala Gly
                20                  25                  30

Asn Gly Ser Ser Glu Val Glu Val Pro Phe Gln Glu Val Trp Gly
            35                  40                  45

Arg Ser Tyr Cys Arg Ala Leu Glu Arg Leu Val Asp Val Val Ser Glu
        50                  55                  60

Tyr Pro Ser Glu Val Glu His Met Phe Ser Pro Ser Cys Val Ser Leu
65                  70                  75                  80

Leu Arg Cys Thr Gly Cys Cys Gly Asp Glu Asp Leu His Cys Val Pro
                85                  90                  95

Val Glu Thr Ala Asn Val Thr Met Gln Leu Leu Lys Ile Arg Ser Gly
            100                 105                 110

Asp Arg Pro Ser Tyr Val Glu Leu Thr Phe Ser Gln His Val Arg Cys
        115                 120                 125

Glu Cys Arg Pro Leu Arg Glu Lys Met Lys Pro Glu Arg Arg Arg Pro
130                 135                 140

Lys Gly Arg Gly Lys Arg Arg Arg Glu Asn Gln Arg Pro Thr Asp Cys
145                 150                 155                 160

His Leu Cys Gly Asp Ala Val Pro Arg Arg
                165                 170

<210> SEQ ID NO 12
<211> LENGTH: 188
<212> TYPE: PRT
<213> ORGANISM: Homo sapiens

<400> SEQUENCE: 12

Met Ser Pro Leu Leu Arg Arg Leu Leu Leu Ala Ala Leu Leu Gln Leu
 1               5                  10                  15

Ala Pro Ala Gln Ala Pro Val Ser Gln Pro Asp Ala Pro Gly His Gln
                20                  25                  30

Arg Lys Val Val Ser Trp Ile Asp Val Tyr Thr Arg Ala Thr Cys Gln
            35                  40                  45

Pro Arg Glu Val Val Val Pro Leu Thr Val Glu Leu Met Gly Thr Val
        50                  55                  60

Ala Lys Gln Leu Val Pro Ser Cys Val Thr Val Gln Arg Cys Gly Gly
65                  70                  75                  80

Cys Cys Pro Asp Asp Gly Leu Glu Cys Val Pro Thr Gly Gln His Gln
                85                  90                  95

Val Arg Met Gln Ile Leu Met Ile Arg Tyr Pro Ser Ser Gln Leu Gly
```

-continued

```
                  100                 105                 110
Glu Met Ser Leu Glu Glu His Ser Gln Cys Glu Cys Arg Pro Lys Lys
                115                 120                 125

Lys Asp Ser Ala Val Lys Pro Asp Ser Pro Arg Pro Leu Cys Pro Arg
130                 135                 140

Cys Thr Gln His His Gln Arg Pro Asp Pro Arg Thr Cys Arg Cys Arg
145                 150                 155                 160

Cys Arg Arg Arg Ser Phe Leu Arg Cys Gln Gly Arg Gly Leu Glu Leu
                165                 170                 175

Asn Pro Asp Thr Cys Arg Cys Arg Lys Leu Arg Arg
                180                 185

<210> SEQ ID NO 13
<211> LENGTH: 364
<212> TYPE: PRT
<213> ORGANISM: Homo sapiens

<400> SEQUENCE: 13

Met Glu Thr Leu Tyr Ser Leu Glu Leu Glu Val Ala Leu Gly Leu Tyr
 1               5                  10                  15

Ile Leu Glu Leu Glu Val Ala Leu Ala Leu Val Ala Leu Cys Tyr
                20                  25                  30

Ser Leu Glu His Ile Ser Gly Leu Asn Thr Tyr Arg Leu Glu Leu Glu
            35                  40                  45

Ala Ser Asn Ala Leu Ala Ala Ser Pro Ser Arg Ala Ser Asn Thr
        50                  55                  60

His Arg Leu Tyr Ser Gly Leu Tyr Thr Arg Pro Ser Glu Arg Gly Leu
65                  70                  75                  80

Val Ala Leu Leu Glu Leu Tyr Ser Gly Leu Tyr Ser Glu Arg Gly Leu
                85                  90                  95

Cys Tyr Ser Leu Tyr Ser Pro Arg Ala Arg Gly Pro Arg Ile Leu Glu
                100                 105                 110

Val Ala Leu Val Ala Leu Pro Arg Val Ala Leu Ser Glu Arg Gly Leu
                115                 120                 125

Thr His Arg His Ile Ser Pro Arg Gly Leu Leu Glu Thr His Arg Ser
            130                 135                 140

Glu Arg Gly Leu Asn Ala Arg Gly Pro His Glu Ala Ser Asn Pro Arg
145                 150                 155                 160

Pro Arg Cys Tyr Ser Val Ala Leu Thr His Arg Leu Glu Met Glu Thr
                165                 170                 175

Ala Arg Gly Cys Tyr Ser Gly Leu Tyr Gly Leu Tyr Cys Tyr Ser Cys
                180                 185                 190

Tyr Ser Ala Ser Asn Ala Ser Pro Gly Leu Ser Glu Arg Leu Glu Gly
            195                 200                 205

Leu Cys Tyr Ser Val Ala Leu Pro Arg Thr His Arg Gly Leu Gly Leu
        210                 215                 220

Val Ala Leu Ala Ser Asn Val Ala Leu Ser Glu Arg Met Glu Thr Gly
225                 230                 235                 240

Leu Leu Glu Leu Glu Gly Leu Tyr Ala Leu Ala Ser Glu Arg Gly Leu
                245                 250                 255

Tyr Ser Glu Arg Gly Leu Tyr Ser Glu Arg Ala Ser Asn Gly Leu Tyr
                260                 265                 270

Met Glu Thr Gly Leu Asn Ala Arg Gly Leu Glu Ser Glu Arg Pro His
            275                 280                 285
```

```
Glu Val Ala Leu Gly Leu His Ile Ser Leu Tyr Ser Leu Tyr Ser Cys
    290                 295                 300

Tyr Ser Ala Ser Pro Cys Tyr Ser Ala Arg Gly Pro Arg Ala Arg Gly
305                 310                 315                 320

Pro His Glu Thr His Arg Thr His Arg Thr His Arg Pro Arg Pro Arg
                325                 330                 335

Thr His Arg Thr His Arg Thr His Arg Ala Arg Gly Pro Arg Pro Arg
            340                 345                 350

Ala Arg Gly Ala Arg Gly Ala Arg Gly Ala Arg Gly
        355                 360

<210> SEQ ID NO 14
<211> LENGTH: 419
<212> TYPE: PRT
<213> ORGANISM: Homo sapiens

<400> SEQUENCE: 14

Met His Leu Leu Gly Phe Phe Ser Val Ala Cys Ser Leu Leu Ala Ala
  1               5                  10                  15

Ala Leu Leu Pro Gly Pro Arg Glu Ala Pro Ala Ala Ala Ala Ala Phe
                20                  25                  30

Glu Ser Gly Leu Asp Leu Ser Asp Ala Glu Pro Asp Ala Gly Glu Ala
            35                  40                  45

Thr Ala Tyr Ala Ser Lys Asp Leu Glu Glu Gln Leu Arg Ser Val Ser
     50                  55                  60

Ser Val Asp Glu Leu Met Thr Val Leu Tyr Pro Glu Tyr Trp Lys Met
 65                  70                  75                  80

Tyr Lys Cys Gln Leu Arg Lys Gly Gly Trp Gln His Asn Arg Glu Gln
                85                  90                  95

Ala Asn Leu Asn Ser Arg Thr Glu Glu Thr Ile Lys Phe Ala Ala Ala
                100                 105                 110

His Tyr Asn Thr Glu Ile Leu Lys Ser Ile Asp Asn Glu Trp Arg Lys
            115                 120                 125

Thr Gln Cys Met Pro Arg Glu Val Cys Ile Asp Val Gly Lys Glu Phe
130                 135                 140

Gly Val Ala Thr Asn Thr Phe Phe Lys Pro Pro Cys Val Ser Val Tyr
145                 150                 155                 160

Arg Cys Gly Gly Cys Cys Asn Ser Glu Gly Leu Gln Cys Met Asn Thr
                165                 170                 175

Ser Thr Ser Tyr Leu Ser Lys Thr Leu Phe Glu Ile Thr Val Pro Leu
            180                 185                 190

Ser Gln Gly Pro Lys Pro Val Thr Ile Ser Phe Ala Asn His Thr Ser
        195                 200                 205

Cys Arg Cys Met Ser Lys Leu Asp Val Tyr Arg Gln Val His Ser Ile
210                 215                 220

Ile Arg Arg Ser Leu Pro Ala Thr Leu Pro Gln Cys Gln Ala Ala Asn
225                 230                 235                 240

Lys Thr Cys Pro Thr Asn Tyr Met Trp Asn Asn His Ile Cys Arg Cys
                245                 250                 255

Leu Ala Gln Glu Asp Phe Met Phe Ser Ser Asp Ala Gly Asp Asp Ser
            260                 265                 270

Thr Asp Gly Phe His Asp Ile Cys Gly Pro Asn Lys Glu Leu Asp Glu
        275                 280                 285

Glu Thr Cys Gln Cys Val Cys Arg Ala Gly Leu Arg Pro Ala Ser Cys
290                 295                 300
```

```
Gly Pro His Lys Glu Leu Asp Arg Asn Ser Cys Gln Cys Val Cys Lys
305                 310                 315                 320

Asn Lys Leu Phe Pro Ser Gln Cys Gly Ala Asn Arg Glu Phe Asp Glu
            325                 330                 335

Asn Thr Cys Gln Cys Val Cys Lys Arg Thr Cys Pro Arg Asn Gln Pro
        340                 345                 350

Leu Asn Pro Gly Lys Cys Ala Cys Glu Cys Thr Glu Ser Pro Gln Lys
    355                 360                 365

Cys Leu Leu Lys Gly Lys Lys Phe His His Gln Thr Cys Ser Cys Tyr
370                 375                 380

Arg Arg Pro Cys Thr Asn Arg Gln Lys Ala Cys Glu Pro Gly Phe Ser
385                 390                 395                 400

Tyr Ser Glu Glu Val Cys Arg Cys Val Pro Ser Tyr Trp Lys Arg Pro
                405                 410                 415

Gln Met Ser

<210> SEQ ID NO 15
<211> LENGTH: 358
<212> TYPE: PRT
<213> ORGANISM: Homo sapiens

<400> SEQUENCE: 15

Met Tyr Gly Glu Trp Gly Met Gly Asn Ile Leu Met Met Phe His Val
1               5                   10                  15

Tyr Leu Val Gln Gly Phe Arg Ser Glu His Gly Pro Val Lys Asp Phe
            20                  25                  30

Ser Phe Glu Arg Ser Ser Arg Ser Met Leu Glu Arg Ser Glu Gln Gln
        35                  40                  45

Ile Arg Ala Ala Ser Ser Leu Glu Glu Leu Leu Gln Ile Ala His Ser
    50                  55                  60

Glu Asp Trp Lys Leu Trp Arg Cys Arg Leu Lys Leu Lys Ser Leu Ala
65                  70                  75                  80

Ser Met Asp Ser Arg Ser Ala Ser His Arg Ser Thr Arg Phe Ala Ala
                85                  90                  95

Thr Phe Tyr Asp Thr Glu Thr Leu Lys Val Ile Asp Glu Glu Trp Gln
            100                 105                 110

Arg Thr Gln Cys Ser Pro Arg Glu Thr Cys Val Glu Val Ala Ser Glu
        115                 120                 125

Leu Gly Lys Thr Thr Asn Thr Phe Phe Lys Pro Pro Cys Val Asn Val
    130                 135                 140

Phe Arg Cys Gly Gly Cys Cys Asn Glu Glu Gly Val Met Cys Met Asn
145                 150                 155                 160

Thr Ser Thr Ser Tyr Ile Ser Lys Gln Leu Phe Glu Ile Ser Val Pro
                165                 170                 175

Leu Thr Ser Val Pro Glu Leu Val Pro Val Lys Ile Ala Asn His Thr
            180                 185                 190

Gly Cys Lys Cys Leu Pro Thr Gly Pro Arg His Pro Tyr Ser Ile Ile
        195                 200                 205

Arg Arg Ser Ile Gln Thr Pro Glu Glu Asp Glu Cys Pro His Ser Lys
    210                 215                 220

Lys Leu Cys Pro Ile Asp Met Leu Trp Asp Asn Thr Lys Cys Lys Cys
225                 230                 235                 240

Val Leu Gln Asp Glu Thr Pro Leu Pro Gly Thr Glu Asp His Ser Tyr
                245                 250                 255
```

```
Leu Gln Glu Pro Thr Leu Cys Gly Pro His Met Thr Phe Asp Glu Asp
            260                 265                 270

Arg Cys Glu Cys Val Cys Lys Ala Pro Cys Pro Gly Asp Leu Ile Gln
        275                 280                 285

His Pro Glu Asn Cys Ser Cys Phe Glu Cys Lys Glu Ser Leu Glu Ser
    290                 295                 300

Cys Cys Gln Lys His Lys Ile Phe His Pro Asp Thr Cys Ser Cys Glu
305                 310                 315                 320

Asp Arg Cys Pro Phe His Thr Arg Thr Cys Ala Ser Arg Lys Pro Ala
                325                 330                 335

Cys Gly Lys His Trp Arg Phe Pro Lys Glu Thr Arg Ala Gln Gly Leu
            340                 345                 350

Tyr Ser Gln Glu Asn Pro
        355
```

<210> SEQ ID NO 16
<211> LENGTH: 211
<212> TYPE: PRT
<213> ORGANISM: Homo sapiens

<400> SEQUENCE: 16

```
Met Arg Thr Leu Ala Cys Leu Leu Leu Gly Cys Gly Tyr Leu Ala
  1               5                  10                  15

His Val Leu Ala Glu Glu Ala Glu Ile Pro Arg Glu Val Ile Glu Arg
                20                  25                  30

Leu Ala Arg Ser Gln Ile His Ser Ile Arg Asp Leu Gln Arg Leu Leu
            35                  40                  45

Glu Ile Asp Ser Val Gly Ser Glu Asp Ser Leu Asp Thr Ser Leu Arg
 50                  55                  60

Ala His Gly Val His Ala Thr Lys His Val Pro Glu Lys Arg Pro Leu
 65                  70                  75                  80

Pro Ile Arg Arg Lys Arg Ser Ile Glu Glu Ala Val Pro Ala Val Cys
                85                  90                  95

Lys Thr Arg Thr Val Ile Tyr Glu Ile Pro Arg Ser Gln Val Asp Pro
                100                 105                 110

Thr Ser Ala Asn Phe Leu Ile Trp Pro Pro Cys Val Glu Val Lys Arg
            115                 120                 125

Cys Thr Gly Cys Cys Asn Thr Ser Ser Val Lys Cys Gln Pro Ser Arg
130                 135                 140

Val His His Arg Ser Val Lys Val Ala Lys Val Glu Tyr Val Arg Lys
145                 150                 155                 160

Lys Pro Lys Leu Lys Glu Val Gln Val Arg Leu Glu Glu His Leu Glu
                165                 170                 175

Cys Ala Cys Ala Thr Thr Ser Leu Asn Pro Asp Tyr Arg Glu Glu Asp
            180                 185                 190

Thr Gly Arg Pro Arg Glu Ser Gly Lys Lys Arg Lys Arg Lys Arg Leu
        195                 200                 205

Lys Pro Thr
    210
```

<210> SEQ ID NO 17
<211> LENGTH: 241
<212> TYPE: PRT
<213> ORGANISM: Homo sapiens

<400> SEQUENCE: 17

```
Met Asn Arg Cys Trp Ala Leu Phe Leu Ser Leu Cys Cys Tyr Leu Arg
 1               5                  10                  15

Leu Val Ser Ala Glu Gly Asp Pro Ile Pro Glu Glu Leu Tyr Glu Met
            20                  25                  30

Leu Ser Asp His Ser Ile Arg Ser Phe Asp Asp Leu Gln Arg Leu Leu
        35                  40                  45

His Gly Asp Pro Gly Glu Glu Asp Gly Ala Glu Leu Asp Leu Asn Met
    50                  55                  60

Thr Arg Ser His Ser Gly Gly Glu Leu Glu Ser Leu Ala Arg Gly Arg
65                  70                  75                  80

Arg Ser Leu Gly Ser Leu Thr Ile Ala Glu Pro Ala Met Ile Ala Glu
                85                  90                  95

Cys Lys Thr Arg Thr Glu Val Phe Glu Ile Ser Arg Arg Leu Ile Asp
            100                 105                 110

Arg Thr Asn Ala Asn Phe Leu Val Trp Pro Pro Cys Val Glu Val Gln
        115                 120                 125

Arg Cys Ser Gly Cys Cys Asn Asn Arg Asn Val Gln Cys Arg Pro Thr
    130                 135                 140

Gln Val Gln Leu Arg Pro Val Gln Val Arg Lys Ile Glu Ile Val Arg
145                 150                 155                 160

Lys Lys Pro Ile Phe Lys Lys Ala Thr Val Thr Leu Glu Asp His Leu
                165                 170                 175

Ala Cys Lys Cys Glu Thr Val Ala Ala Ala Arg Pro Val Thr Arg Ser
            180                 185                 190

Pro Gly Gly Ser Gln Glu Gln Arg Ala Lys Thr Pro Gln Thr Arg Val
        195                 200                 205

Thr Ile Arg Thr Val Arg Val Arg Arg Pro Pro Lys Gly Lys His Arg
    210                 215                 220

Lys Phe Lys His Thr His Asp Lys Thr Ala Leu Lys Glu Thr Leu Gly
225                 230                 235                 240

Ala

<210> SEQ ID NO 18
<211> LENGTH: 121
<212> TYPE: PRT
<213> ORGANISM: Homo sapiens

<400> SEQUENCE: 18

Ser Tyr His Asp Arg Lys Ser Lys Val Asp Leu Asp Arg Leu Asn Asp
 1               5                  10                  15

Asp Ala Lys Arg Tyr Ser Cys Thr Pro Arg Asn Tyr Ser Val Asn Ile
            20                  25                  30

Arg Glu Glu Leu Lys Leu Ala Asn Val Val Phe Phe Pro Arg Cys Leu
        35                  40                  45

Leu Val Gln Arg Cys Gly Gly Asn Cys Gly Cys Gly Thr Val Lys Leu
    50                  55                  60

Glu Ser Cys Thr Cys Asn Ser Gly Lys Thr Val Lys Lys Tyr His Glu
65                  70                  75                  80

Val Leu Gln Phe Glu Pro Gly His Ile Lys Arg Arg Gly Arg Ala Lys
                85                  90                  95

Thr Met Ala Leu Val Asp Ile Gln Leu Asp His His Glu Arg Cys Asp
            100                 105                 110

Cys Ile Cys Ser Ser Arg Pro Pro Arg
        115                 120
```

<210> SEQ ID NO 19
<211> LENGTH: 119
<212> TYPE: PRT
<213> ORGANISM: Homo sapiens

<400> SEQUENCE: 19

Arg Asp Glu Thr Ile Gln Val Lys Gly Asn Gly Tyr Val Gln Ser Pro
 1               5                  10                  15

Arg Phe Pro Asn Ser Tyr Pro Arg Asn Leu Leu Leu Thr Trp Arg Leu
                20                  25                  30

His Ser Gln Glu Asn Thr Arg Ile Gln Leu Val Phe Asp Asn Gln Phe
            35                  40                  45

Gly Leu Glu Glu Ala Glu Asn Asp Ile Cys Arg Tyr Asp Phe Val Glu
 50                  55                  60

Val Glu Asp Ile Ser Glu Thr Ser Thr Ile Ile Arg Gly Arg Trp Cys
 65                  70                  75                  80

Gly His Lys Glu Val Pro Pro Arg Ile Lys Ser Arg Thr Asn Gln Ile
                85                  90                  95

Lys Ile Thr Phe Lys Ser Asp Asp Tyr Phe Val Ala Lys Pro Gly Phe
            100                 105                 110

Lys Ile Tyr Tyr Ser Leu Leu
        115

<210> SEQ ID NO 20
<211> LENGTH: 113
<212> TYPE: PRT
<213> ORGANISM: Homo sapiens

<400> SEQUENCE: 20

Cys Gly Glu Thr Leu Gln Asp Ser Thr Gly Asn Phe Ser Ser Pro Glu
 1               5                  10                  15

Tyr Pro Asn Gly Tyr Ser Ala His Met His Cys Val Trp Arg Ile Ser
                20                  25                  30

Val Thr Pro Gly Glu Lys Ile Ile Leu Asn Phe Thr Ser Leu Asp Leu
            35                  40                  45

Tyr Arg Ser Arg Leu Cys Trp Tyr Asp Tyr Val Glu Val Arg Asp Gly
 50                  55                  60

Phe Trp Arg Lys Ala Pro Leu Arg Gly Arg Phe Cys Gly Ser Lys Leu
 65                  70                  75                  80

Pro Glu Pro Ile Val Ser Thr Asp Ser Arg Leu Trp Val Glu Phe Arg
                85                  90                  95

Ser Ser Ser Asn Trp Val Gly Lys Gly Phe Phe Ala Val Tyr Glu Ala
            100                 105                 110

Ile

<210> SEQ ID NO 21
<211> LENGTH: 112
<212> TYPE: PRT
<213> ORGANISM: Homo sapiens

<400> SEQUENCE: 21

Cys Gly Gly Asp Val Lys Lys Asp Tyr Gly His Ile Gln Ser Pro Asn
 1               5                  10                  15

Tyr Pro Asp Asp Tyr Arg Pro Ser Lys Val Cys Ile Trp Arg Ile Gln
                20                  25                  30

Val Ser Glu Gly Phe His Val Gly Leu Thr Phe Gln Ser Phe Glu Ile

```
              35                  40                  45
Glu Arg Met Asp Ser Cys Ala Tyr Asp Tyr Leu Glu Val Arg Asp Gly
     50                  55                  60

His Ser Glu Ser Ser Thr Leu Ile Gly Arg Tyr Cys Gly Tyr Glu Lys
 65                  70                  75                  80

Pro Asp Asp Ile Lys Ser Thr Ser Ser Arg Leu Trp Leu Lys Phe Val
                 85                  90                  95

Ser Asp Gly Ser Ile Asn Lys Ala Gly Phe Ala Val Asn Phe Phe Lys
            100                 105                 110

<210> SEQ ID NO 22
<211> LENGTH: 113
<212> TYPE: PRT
<213> ORGANISM: Homo sapiens

<400> SEQUENCE: 22

Cys Gly Gly Phe Leu Thr Lys Leu Asn Gly Ser Ile Thr Ser Pro Gly
  1               5                  10                  15

Trp Pro Lys Glu Tyr Pro Pro Asn Lys Asn Cys Ile Trp Gln Leu Val
             20                  25                  30

Ala Pro Thr Gln Tyr Arg Ile Ser Leu Gln Phe Asp Phe Phe Glu Thr
         35                  40                  45

Glu Gly Asn Asp Val Cys Lys Tyr Asp Phe Val Glu Val Arg Ser Gly
     50                  55                  60

Leu Thr Ala Asp Ser Lys Leu His Gly Lys Phe Cys Gly Ser Glu Lys
 65                  70                  75                  80

Pro Glu Val Ile Thr Ser Gln Tyr Asn Asn Met Arg Val Glu Pro Lys
                 85                  90                  95

Ser Asp Asn Thr Val Ser Lys Lys Gly Phe Lys Ala His Phe Phe Ser
            100                 105                 110

Glu

<210> SEQ ID NO 23
<211> LENGTH: 113
<212> TYPE: PRT
<213> ORGANISM: Homo sapiens

<400> SEQUENCE: 23

Gly Asp Thr Ile Lys Ile Glu Ser Pro Gly Tyr Leu Thr Ser Pro Gly
  1               5                  10                  15

Tyr Pro His Ser Tyr His Pro Ser Glu Lys Cys Glu Trp Leu Ile Gln
             20                  25                  30

Ala Pro Asp Pro Tyr Gln Arg Ile Met Ile Asn Phe Asn Pro His Phe
         35                  40                  45

Asp Leu Glu Asp Arg Asp Cys Lys Tyr Asp Tyr Val Glu Val Phe Asp
     50                  55                  60

Gly Glu Asn Glu Asn Gly His Phe Arg Gly Lys Phe Cys Gly Lys Ile
 65                  70                  75                  80

Ala Pro Pro Pro Val Val Ser Ser Gly Pro Phe Leu Phe Ile Lys Phe
                 85                  90                  95

Val Ser Asp Tyr Glu Thr His Gly Ala Gly Phe Ser Ile Arg Tyr Glu
            100                 105                 110

Ile

<210> SEQ ID NO 24
<211> LENGTH: 119
```

```
<212> TYPE: PRT
<213> ORGANISM: Homo sapiens

<400> SEQUENCE: 24

Cys Ser Gln Asn Tyr Thr Thr Pro Ser Gly Val Ile Lys Ser Pro Gly
 1               5                  10                  15

Phe Pro Glu Lys Tyr Pro Asn Ser Leu Glu Cys Thr Tyr Ile Val Phe
            20                  25                  30

Ala Pro Lys Met Ser Glu Ile Ile Leu Glu Phe Glu Ser Phe Asp Leu
        35                  40                  45

Glu Pro Asp Ser Asn Pro Pro Gly Gly Met Phe Cys Arg Tyr Asp Arg
    50                  55                  60

Leu Glu Ile Trp Asp Gly Phe Pro Asp Val Gly Pro His Ile Gly Arg
65                  70                  75                  80

Tyr Cys Gly Gln Lys Thr Pro Gly Arg Ile Arg Ser Ser Gly Ile
                85                  90                  95

Leu Ser Met Val Phe Tyr Thr Asp Ser Ala Ile Ala Lys Glu Gly Phe
            100                 105                 110

Ser Ala Asn Tyr Ser Val Leu
        115

<210> SEQ ID NO 25
<211> LENGTH: 15
<212> TYPE: PRT
<213> ORGANISM: Homo sapiens

<400> SEQUENCE: 25

Pro Xaa Cys Leu Leu Val Xaa Arg Cys Gly Gly Asn Cys Xaa Cys
 1               5                  10                  15

<210> SEQ ID NO 26
<211> LENGTH: 20
<212> TYPE: DNA
<213> ORGANISM: Homo sapiens

<400> SEQUENCE: 26
gtcgtggaac tgtcaactgg                                                   20

<210> SEQ ID NO 27
<211> LENGTH: 20
<212> TYPE: DNA
<213> ORGANISM: Homo sapiens

<400> SEQUENCE: 27
ctcagcaacc acttgtgttc                                                   20

<210> SEQ ID NO 28
<211> LENGTH: 27
<212> TYPE: DNA
<213> ORGANISM: Homo sapiens

<400> SEQUENCE: 28
ccatcctaat acgactcact atagggc                                           27

<210> SEQ ID NO 29
<211> LENGTH: 29
<212> TYPE: DNA
<213> ORGANISM: Homo sapiens

<400> SEQUENCE: 29
agtgggatcc gttactgatg gagagttat                                         29
```

```
<210> SEQ ID NO 30
<211> LENGTH: 26
<212> TYPE: DNA
<213> ORGANISM: Homo sapiens

<400> SEQUENCE: 30
cccaagcttg aagatcttga gaatat                                          26

<210> SEQ ID NO 31
<211> LENGTH: 22
<212> TYPE: DNA
<213> ORGANISM: Homo sapiens

<400> SEQUENCE: 31
tgctctagat cgaggtggtc tt                                              22
```